United States Patent
Barnes et al.

(10) Patent No.: US 9,976,105 B2
(45) Date of Patent: *May 22, 2018

(54) SILICONE POLYMER EMULSIONS

(75) Inventors: Kathleen Barnes, Midland, MI (US); Jary David Jensen, Beaverton, MI (US); Walker L. Rochlitz, Midland, MI (US); Andreas Stammer, Pont-a Celles (BE)

(73) Assignee: DOW SILICONES CORPORATION, Midland, MI (US)

( * ) Notice: Subject to any disclaimer, the term of this patent is extended or adjusted under 35 U.S.C. 154(b) by 1681 days.

This patent is subject to a terminal disclaimer.

(21) Appl. No.: 12/445,102

(22) PCT Filed: Oct. 9, 2007

(86) PCT No.: PCT/US2007/021562
§ 371 (c)(1),
(2), (4) Date: Dec. 21, 2009

(87) PCT Pub. No.: WO2008/045427
PCT Pub. Date: Apr. 17, 2008

(65) Prior Publication Data
US 2010/0137454 A1 Jun. 3, 2010

Related U.S. Application Data

(60) Provisional application No. 60/828,864, filed on Oct. 10, 2006.

(51) Int. Cl.
| | |
|---|---|
| C10M 155/02 | (2006.01) |
| A61K 8/06 | (2006.01) |
| A61K 8/891 | (2006.01) |
| A61Q 19/00 | (2006.01) |
| C08J 3/03 | (2006.01) |
| C10M 107/50 | (2006.01) |
| C10M 173/02 | (2006.01) |
| C11D 3/37 | (2006.01) |
| D06M 15/643 | (2006.01) |
| A61Q 1/10 | (2006.01) |
| A61Q 5/02 | (2006.01) |
| A61Q 5/12 | (2006.01) |
| A61Q 19/10 | (2006.01) |

(52) U.S. Cl.
CPC ........... *C10M 155/02* (2013.01); *A61K 8/062* (2013.01); *A61K 8/068* (2013.01); *A61K 8/891* (2013.01); *A61Q 19/00* (2013.01); *C08J 3/03* (2013.01); *C10M 107/50* (2013.01); *C10M 173/02* (2013.01); *C11D 3/373* (2013.01); *D06M 15/643* (2013.01); *A61Q 1/10* (2013.01); *A61Q 5/02* (2013.01); *A61Q 5/12* (2013.01); *A61Q 19/10* (2013.01); *C08J 2383/04* (2013.01); *C10M 2229/04* (2013.01); *C10M 2229/041* (2013.01); *C10M 2229/043* (2013.01); *C10M 2229/045* (2013.01); *C10M 2229/0405* (2013.01); *C10M 2229/0415* (2013.01); *C10M 2229/0435* (2013.01); *C10M 2229/0455* (2013.01)

(58) Field of Classification Search
CPC ....... A61K 8/062; C10M 155/02; A11D 3/373
See application file for complete search history.

(56) References Cited

U.S. PATENT DOCUMENTS

| | | | |
|---|---|---|---|
| 2,891,920 | A | 6/1959 | Hyde et al. |
| 3,294,725 | A | 12/1966 | Findlay et al. |
| 3,419,593 | A | 12/1968 | Williing |
| 3,445,420 | A | 5/1969 | Kookootsedes et al. |
| 3,715,334 | A | 2/1973 | Karstedt |
| 3,814,730 | A | 6/1974 | Karstedt |
| 3,819,530 | A | 6/1974 | Ratledge et al. |
| 3,839,388 | A | 10/1974 | Nitzsche |
| 3,923,705 | A | 12/1975 | Smith |

(Continued)

FOREIGN PATENT DOCUMENTS

| | | |
|---|---|---|
| CN | 1230547 A | 10/1999 |
| EP | 0200916 A2 | 11/1986 |

(Continued)

OTHER PUBLICATIONS

English language abstract for EP 0215470 extracted from espacenet.com database, dated Aug. 17, 2009, 14 pages.
English language translation and abstract for JP 2000-026726 extracted from PAJ database, dated Aug. 17, 2009, 48 pages.
PCT International Search Report for PCT/EP2007/008753, dated May 15, 2008, 4 pages.
PCT International Search Report for PCT/US2007/021562, dated Feb. 8, 2008, 4 pages.

(Continued)

*Primary Examiner* — Kyle A Purdy
(74) *Attorney, Agent, or Firm* — Warner Norcross & Judd LLP

(57) ABSTRACT

Silicone oil-in-water emulsions containing a polysiloxane containing polymer is prepared by first preparing a polysiloxane containing polymer by the polymerization of siloxane containing monomers and/or oligomers in the presence of an inert organopoly siloxane and/or an organic fluid, a suitable catalyst and optionally an end-blocking agent; and quenching the reaction if required. If required one or more surfactants may be introduced into the polysiloxane containing polymer to form a homogenous oil phase. Water is then added (in an amount of 0.1-10 percent by weight based on total oil phase weight) to the homogenous oil phase to form a water-in-oil emulsion. Shear is applied to the water-in-oil emulsion to cause inversion of the water-in-oil emulsion to an oil-in-water emulsion. Finally, if required the oil-in-water emulsion can be diluted by adding more water.

16 Claims, No Drawings

(56) References Cited

U.S. PATENT DOCUMENTS

| | | | |
|---|---|---|---|
| 3,989,667 A | 11/1976 | Lee et al. | |
| 4,311,695 A | 1/1982 | Starch | |
| 4,312,801 A | 1/1982 | Hiriart Bodin et al. | |
| 4,404,035 A | 9/1983 | Ona et al. | |
| 4,564,693 A | 1/1986 | Riederer | |
| 4,614,758 A | 9/1986 | Schwabe et al. | |
| 4,701,490 A | 10/1987 | Burkhardt et al. | |
| 4,725,658 A | 2/1988 | Thayer et al. | |
| 4,788,001 A | 11/1988 | Narula | |
| 4,990,556 A | 2/1991 | Shimizu et al. | |
| 4,990,561 A | 2/1991 | Yoshioka | |
| 5,035,832 A | 7/1991 | Takamura et al. | |
| 5,039,724 A | 8/1991 | Demlehner et al. | |
| 5,133,897 A | 7/1992 | Balzer | |
| 5,175,325 A | 12/1992 | Brown et al. | |
| 5,189,102 A | 2/1993 | Tsubuko et al. | |
| 5,262,087 A | 11/1993 | Tachibana et al. | |
| 5,403,909 A | 4/1995 | Rubinsztajn | |
| 5,424,385 A | 6/1995 | Hager et al. | |
| 5,434,215 A | 7/1995 | Sankaran et al. | |
| 5,457,220 A | 10/1995 | Razzano | |
| 5,503,755 A | 4/1996 | Danner | |
| 5,504,150 A * | 4/1996 | Gilson et al. | 524/837 |
| 5,603,940 A | 2/1997 | Candau et al. | |
| 5,633,303 A | 5/1997 | Kondo et al. | |
| 5,830,483 A | 11/1998 | Seidel et al. | |
| 5,888,485 A | 3/1999 | O'Lenick, Jr. et al. | |
| 5,914,362 A | 6/1999 | Brecht et al. | |
| 5,925,469 A | 7/1999 | Gee et al. | |
| 5,973,068 A | 10/1999 | Yamaya et al. | |
| 6,001,928 A | 12/1999 | Harkness et al. | |
| 6,048,819 A | 4/2000 | Habimana | |
| 6,054,548 A | 4/2000 | Currie et al. | |
| 6,258,891 B1 | 7/2001 | Hoxmeier | |
| 6,328,983 B1 | 12/2001 | Afriat | |
| 6,362,280 B1 | 3/2002 | Lences et al. | |
| 6,448,196 B1 | 9/2002 | Eglin et al. | |
| 6,468,513 B1 | 10/2002 | Murphy et al. | |
| 6,737,444 B1 * | 5/2004 | Liu | 516/55 |
| 6,878,773 B2 * | 4/2005 | Marteaux et al. | 524/837 |
| 7,041,088 B2 | 5/2006 | Nawrocki et al. | |
| 7,754,800 B2 | 7/2010 | Maton et al. | |
| 8,022,162 B2 | 9/2011 | Maton et al. | |
| 2003/0191244 A1 | 10/2003 | Yu | |
| 2004/0210074 A1* | 10/2004 | Hupfield et al. | 556/413 |
| 2005/0143282 A1 | 6/2005 | Creutz et al. | |
| 2006/0104929 A1* | 5/2006 | Morita et al. | 424/70.12 |
| 2008/0114143 A1 | 5/2008 | Brothers et al. | |
| 2009/0042043 A1 | 2/2009 | Joseph et al. | |
| 2009/0215944 A1* | 8/2009 | Maton et al. | 524/413 |
| 2010/0093598 A1 | 4/2010 | Davio et al. | |
| 2010/0137454 A1 | 6/2010 | Barmes et al. | |
| 2012/0027708 A1 | 2/2012 | Durand et al. | |
| 2012/0077729 A1 | 3/2012 | Davio et al. | |
| 2012/0269875 A1 | 10/2012 | Tamura et al. | |

FOREIGN PATENT DOCUMENTS

| | | |
|---|---|---|
| EP | 0215470 A2 | 3/1987 |
| EP | 0382365 A2 | 8/1990 |
| EP | 0722972 A1 | 7/1996 |
| EP | 0736562 A2 | 10/1996 |
| EP | 0802231 A2 | 10/1997 |
| EP | 0842974 A1 | 5/1998 |
| EP | 1029897 A2 | 8/2000 |
| EP | 1314415 A1 | 5/2003 |
| EP | 1447423 A1 | 8/2004 |
| EP | 1466935 A1 | 10/2004 |
| EP | 1557435 A1 | 7/2005 |
| EP | 1671673 A1 | 6/2006 |
| EP | 1646696 B1 | 5/2010 |
| GB | 803289 A | 10/1958 |
| GB | 895091 A | 5/1962 |
| GB | 918823 A | 2/1963 |
| GB | 2252975 A | 8/1992 |
| JP | H06-345874 A | 12/1994 |
| JP | H07-149774 A | 6/1995 |
| JP | 8325456 A | 12/1996 |
| JP | H08-325456 A | 12/1996 |
| JP | 11-222554 A | 8/1999 |
| JP | 2000026726 A | 1/2000 |
| JP | 2006-515383 A | 5/2006 |
| JP | 2008-534770 A | 8/2008 |
| JP | 2008-535968 A | 9/2008 |
| JP | 2011-071522 A | 4/2011 |
| WO | WO 01/25389 A1 | 4/2001 |
| WO | WO 0149774 A2 | 7/2001 |
| WO | WO 0149789 A2 | 7/2001 |
| WO | WO 0179330 A1 | 10/2001 |
| WO | WO 03/000206 A2 | 1/2003 |
| WO | WO 03/082356 A2 | 10/2003 |
| WO | WO 2004/084844 A2 | 10/2004 |
| WO | WO 2005016998 A2 | 2/2005 |
| WO | WO 2006106362 A1 | 10/2006 |
| WO | WO 2008/045427 A1 | 4/2008 |
| WO | WO 2008043512 A2 | 4/2008 |
| WO | WO 2008/110590 A1 | 9/2008 |
| WO | WO 2010/115783 A2 | 10/2010 |

OTHER PUBLICATIONS

English language abstract and machine-assisted English translation for JP 2011-071522 extracted from the PAJ database on Oct. 10, 2013, 174 pages.

English language abstract and machine-assisted English translation for WO 03/000206 extracted from the espacenet.com database on Oct. 31, 2013, 54 pages.

English language abstract not available for CN 1230547; however, see English language equivalent U.S. Pat. No. 6,048,819. Original document extracted from the espacenet.com database on Jul. 8, 2013, 9 pages.

English language abstract not available for JP H08-325456; however, see English language equivalent U.S. Pat. No. 5,504,150. Original document extracted from the espacenet.com database on Jul. 8, 2013, 12 pages.

English language abstract and machine-assisted English translation for JP 11-222554 extracted from the PAJ database on Jul. 8, 2013, 36 pages.

English language abstract not available for JP 2006-515383; however, see English language equivalent U.S. Pat. No. 6,737,444. Original document extracted from the espacenet.com database on Jul. 8, 2013, 15 pages.

H.H. Chuah et al., "Poly(trimethylene terephthalate) molecular weight and Mark-Houwink equation", Polymer 42 (2001) 7137-7139.

International Search Report for Application No. PCT/EP2007/054219 dated Sep. 14, 2007, 4 pages.

International Search Report for Application No. PCT/EP2007/060586 dated Jun. 4, 2008, 3 pages.

International Search Report for Application No. PCT/US2007/021562 dated Feb. 8, 2008, 3 pages.

International Search Report for Application No. PCT/EP2010/054220 dated Oct. 4, 2010, 4 pages.

International Search Report for Application No. PCT/EP2010/054221 dated Jan. 14, 2011, 6 pages.

English language abstract not available for JP H06-345874; however, see English language equivalent U.S. Pat. No. 5,424,385. Original document extracted from the espacenet.com database on Feb. 21, 2014, 16 pages.

English language abstract and machine-assisted English translation for JP H07-149774 extracted from the PAJ database on Feb. 21, 2014, 42 pages.

English language abstract not available for JP 2008-534770; however, see English language equivalent U.S. Pat. No. 8,022,162. Original document extracted from the espacenet.com database on Feb. 21, 2014, 43 pages.

English language abstract not available for JP 2008-535968; however, see English language equivalent U.S. Pat. No. 7,754,800. Original document extracted from the espacenet.com database on Feb. 21, 2014, 54 pages.

(56) References Cited

OTHER PUBLICATIONS

English language abstract not available for JP 8325456; however, see English language equivalent U.S. Pat. No. 5,504,150. Original Document extracted from the espacenet.com database on Nov. 12, 2012, 12 pages.
English language abstract and translation for JP 11-222554 extracted from the PAJ database on Nov. 12, 2012, 36 pages.
English language abstract not available for JP 2006-515383; however, see English language equivalent U.S. Pat. No. 6,737,444. Original Document extracted from the espacenet.com database on Nov. 12, 2012, 15 pages.

* cited by examiner

SILICONE POLYMER EMULSIONS

RELATED APPLICATIONS

This application claims priority to and all the advantages of International Patent Application No. PCT/US2007/021562, filed on Oct. 9, 2007, which claims priority to U.S. Provisional Patent Application No. 60/828,864, filed on Oct. 10, 2006.

This invention relates to silicone in water emulsions, methods of making said emulsions and their uses.

Silicone emulsions are well known in the art. Such silicone emulsions can be made by processes such as (i) mechanical emulsification, (ii) mechanical emulsification by inversion, or by (iii) emulsion polymerization. However, because of the high viscosity of some silicones such as silicone gums, their emulsification has for all practical purposes been limited to emulsion polymerization. In contrast, silicones with a low viscosity and hence a low molecular weight can easily be obtained mechanically.

Attempts to use mechanical methods for emulsifying high molecular weight and viscosity organopolysiloxane polymers, often referred to as silicone gums, have largely been unsuccessful, because it is difficult to incorporate a surfactant or a mixture of surfactants into the polymer because of the viscosity of the polymer. It is also difficult to incorporate water into mixtures containing high viscosity silicones, a surfactant, or a mixture of surfactants, and at the same time impart sufficient shear to cause inversion. In addition, the control of particle size has been limited to processes involving batch-wise mechanical emulsification in the presence of a volatile solvent which is substantially removed during the polymerisation process.

In contrast to the above, the present invention provides an inexpensive technique for producing stable emulsions comprising silicone polymers including polymers which if traditionally prepared would have the viscosity of a silicone gum or like high viscosity polymers.

Whilst the present application relates to organopolysiloxane polymers having a viscosity when prepared traditionally of greater than 50 000 mPa·s at 25° C. being used to prepare emulsions it is considered particularly pertinent to organopolysiloxane polymers of very high viscosity, known in the industry as Silicone gums (e.g. viscosity of about 1 000 000 mPa·s at 25° C. or greater). Silicone gums are high molecular weight generally linear or branched polydiorganosiloxanes that can be converted from their highly viscous plastic state into a predominately elastic state by crosslinking. Silicone gums are often used as one of the main components in the preparation of silicone elastomers and silicone rubbers.

For purposes of this invention therefore, silicone gum can be considered to describe stiff gum-like organosiloxane polymer having a degree of polymerisation equal to or greater than 1500. These polymers are preferably substantially linear, most preferably completely linear and have a viscosity which is sufficiently high to render direct viscosity very difficult and as such are often referred to in terms of their Williams plasticity number. Gums typically have a Williams plasticity number (ASTM D926) in the range of from about 30 to 250 (the thickness in millimeters×100 of a cylindrical test specimen 2 cubic cm in volume and approximately 10 mm in height after the specimen has been subjected to a compressive load of 49 Newtons for three minutes at 25° C.

The two main routes to emulsifying high molecular weight silicones are emulsion polymerisation or the dilution of pre-formed high molecular weight polymers with low molecular weight silicone fluids such as cyclic siloxanes comprising between 2 and 20 silicon atoms. Proceeding down either of these routes can lead to a number of processing problems which are extremely difficult to overcome. In the case of emulsion polymerisation it is exceptionally difficult to control the molecular weight of the end product and indeed viscosities resulting from such processes are so high that there is typically no absolute means of measuring the viscosity of the product manufactured via this route. It is also difficult to achieve a truly continuous process. Preformed siloxane polymers having very high viscosities (viscosity greater than 1 000 000 mPa·s at 25° C.) are very difficult to dilute because it is very difficult to get lower weight compounds to blend in to the high molecular weight polymer.

U.S. Pat. No. 5,973,068 discusses the emulsion polymerisation of a silanol-terminated resin and a vinyl monomer. Polymerization in the emulsion polymerization process occurs at the silicone water interface so that the rate of polymerization is faster with smaller particles because of the larger surface area. Thus, it is impossible to produce large particle size, high molecular weight silicone gum in water emulsions by emulsion polymerisation.

EP1646696 describes a method of making a silicone oil-in-water emulsion comprising the steps of forming a homogeneous oil phase containing a silicone gum, or the like in the homogenous oil phase mixing one or more surfactants with the homogenous oil phase; adding water to the homogenous oil phase to form a water-in-oil emulsion containing a continuous phase and a dispersed phase, the water being added in an amount of about 0.5-10 percent by weight based on the weight of the silicone in the homogenous oil phase; applying high shear to the water-in-oil emulsion in a twin-screw extruder having a length to diameter L/D ratio of at least 15, to cause inversion of the water-in-oil emulsion to an oil-in-water emulsion; and diluting the oil-in-water emulsion by the addition of water.

EP1447423 describes a process for the production of a silicone in water emulsion in which a polysiloxane fluid, at least one surfactant and water are continuously fed to a high shear mixer in such proportions as to form a viscous oil in water emulsion which is continuously withdrawn from the mixer. The polysiloxane fluid may be a non-reactive fluid or may have reactive groups capable of taking part in a chain extension reaction.

The invention is directed to a method of making silicone oil-in-water emulsions containing a polysiloxane containing polymer comprising the steps of i) Preparing a polysiloxane containing polymer by the polymerisation of siloxane containing monomers and/or oligomers in the presence of an inert organopolysiloxane and/or an organic fluid, a suitable catalyst and optionally an end-blocking agent; and ii) Where required quenching the polymerisation process; wherein the inert fluid is substantially retained within the resulting diluted polysiloxane containing polymer (iii) if required, introducing one or more surfactants into the polysiloxane containing polymer to form a homogenous oil phase;

(iv) adding water to the homogenous oil phase to form a water-in-oil emulsion containing a continuous phase and a dispersed phase, (v) applying shear to the water-in-oil emulsion to cause inversion of the water-in-oil emulsion to an oil-in-water emulsion; and optionally (vi) diluting the oil-in-water emulsion by adding more water.

The concept of "comprising" where used herein is used in its widest sense to mean and to encompass the notions of "include" and "consist of". All viscosity measurements referred to herein were measured at 25° C. unless otherwise indicated.

For the sake of this application an inert fluid a substantially non-volatile fluid which is intended to be unreactive towards any other constituent i.e. it does not chemically participate in the polymerisation reaction of step (i) or chemically interact with the additives introduced in any of steps (i) through to (vi). The inert fluid is not removed prior to emulsification. Hence the inert fluid is substantially present in the emulsion.

A polysiloxane containing polymer is intended to mean a polymer comprising multiple organosiloxane or polyorganosiloxane groups per molecule and is intended to include a polymer substantially containing only organosiloxane or polyorganosiloxane groups in the polymer chain and polymers where the backbone contains both organosiloxane and/or polyorganosiloxane groups and e.g. organic polymeric groups in the polymeric chain. Such polymers can be homopolymers or co-polymers, including, but not limited to, block co-polymers and random co-polymers.

In accordance with the present invention a polysiloxane containing polymer is polymerised in the presence of an inert fluid preferably has the general formula:

$$R_{(3-a)}R^1{}_a SiO[(R_2SiO)_b(RR^1SiO)_c]SiR_{(3-a)}R^1{}_a \qquad (1)$$

wherein each R is the same or different and is an alkyl group containing 1-8 carbon atoms, a substituted alkyl group containing 1 to 6 carbon atoms or an optionally substituted phenyl group; $R^1$ is hydrogen, a hydroxy group, a hydrolysable group, an unsaturated organic group; a is zero or 1, b is an integer and c is zero or an integer and the sum of b+c is equal to a value of at least 200 preferably at least 500, more preferably at least 1500. Such a polymer may comprise a degree of branching (preferably less than 10%, more preferably less that 2%).

For the purpose of this application "Substituted", when used in relation to hydrocarbon groups, means one or more hydrogen atoms in the hydrocarbon group has been replaced with another substituent. Examples of such substituents include, but are not limited to, halogen atoms such as chlorine, fluorine, bromine, and iodine; halogen atom containing groups such as chloromethyl, perfluorobutyl, trifluoroethyl, and nonafluorohexyl; oxygen atoms; oxygen atom containing groups such as (meth)acrylic and carboxyl; nitrogen atoms; nitrogen atom containing groups such as amines, amino-functional groups, amido-functional groups, and cyano-functional groups; sulphur atoms; and sulphur atom containing groups such as mercapto groups.

The polymeric chain may comprise blocks made from chains of units depicted in Formula (1) above where the two R groups or R and $R^1$ groups are:— both alkyl groups (preferably both methyl or ethyl), or
alkyl and phenyl groups, or
alkyl and fluoropropyl, or
alkyl and vinyl or
alkyl and hydrogen groups.

Typically at least one block will comprise siloxane units in which both R groups are alkyl groups.

Whilst preferably the polysiloxane containing polymer has a substantially organopolysiloxane molecular chain, the polysiloxane containing polymer may alternatively contain a block copolymeric backbone comprising at least one block of siloxane groups and an organic component comprising any suitable organic based polymer backbone for example the organic polymer backbone may comprise, for example, polystyrene and/or substituted polystyrenes such as poly(α-methylstyrene), poly(vinylmethylstyrene), dienes, poly(p-trimethylsilylstyrene) and poly(p-trimethylsilyl-α-methylstyrene). Other organic components which may be incorporated in the polymeric backbone may include acetylene terminated oligophenylenes, vinylbenzyl terminated aromatic polysulphones oligomers, aromatic polyesters; aromatic polyester based monomers, polyalkylenes, polyurethanes, aliphatic polyesters, aliphatic polyamides and aromatic polyamides and the like.

However perhaps the most preferred organic based polymeric blocks in polysiloxane containing polymer are polyoxyalkylene based blocks. The oxyalkylene units are not necessarily identical throughout the polyoxyalkylene monomer, but can differ from unit to unit. A polyoxyalkylene block, for example, can be comprised of oxyethylene units, ($-C_2H_4-O-$); oxypropylene units ($-C_3H_6-O-$); or oxybutylene units, ($-C_4H_8-O-$); or mixtures thereof. Preferably the polyoxyalkylene polymeric backbone consists essentially of oxyethylene units and/or oxypropylene units.

Other polyoxyalkylene blocks in the polysiloxane containing polymer may include for example units of the structure—

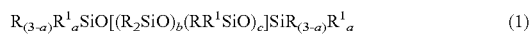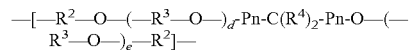

in which Pn is a 1,4-phenylene group, each $R^2$ is the same or different and is a divalent hydrocarbon group having 2 to 8 carbon atoms, each $R^3$ is the same or different and, is, an ethylene group propylene group or isopropylene group, each $R^4$ is the same or different and is a hydrogen atom or methyl group and each of the subscripts d and e is a positive integer in the range from 3 to 30.

Preferably the inert fluid is selected from an organopolysiloxane extender and/or plasticiser and/or an organic extender or plasticiser or a cyclic siloxane comprising between 3 and 20 silicon atoms. Preferably the inert fluid has a viscosity of from 0.65 mPa·s at 25° C.-10000 mPa·s at 25° C.

For the sake of this application an extender (sometimes also referred to as a process aid or secondary plasticiser) is a compound typically used to dilute e.g. silicone based product to make the product more economically competitive without substantially negatively affecting the properties of the sealant formulation.

A plasticiser (otherwise referred to as a primary plasticiser) is added to silicone based compositions to provide properties within the final polymer based product to increase the flexibility and toughness of cured elastomers. This is generally achieved by reduction of the glass transition temperature ($T_g$) of the cured polymer composition thereby e.g. enhancing the elasticity of the elastomer (e.g. a sealant). Plasticisers tend to be generally less volatile than extenders.

Suitable inert liquids include trialkylsilyl terminated polydialkylsiloxanes and derivatives thereof which may comprise a degree of substitution, with the provision that any substituted groups in the inert fluid do not participate in the polymerisation reaction. The substituted groups on the inert fluid are preferably the same as those identified in the previous definition of substituted groups with respect to hydrocarbon groups. Preferably each alkyl group may be the same or different and comprises from 1 to 8 carbon atoms but is preferably a methyl or ethyl group, preferably with a viscosity of from 0.65 to 100 000 mPa·s at 25° C. and most preferably from 10 to 1000 mPa·s at 25° C.

The inert fluid may comprise any suitable organic extender/organic plasticiser. Mineral oil extenders and plasticisers are however particularly preferred. Examples include linear or branched mono unsaturated hydrocarbons such as linear or branched alkenes or mixtures thereof containing at least 12, e.g. from 12 to 25 carbon atoms; and/or mineral oil fractions comprising linear (e.g. n-paraffinic) mineral oils, branched (iso-paraffinic) mineral oils, cyclic (referred in some prior art as naphthenic) mineral oils and mixtures thereof. Preferably the hydrocarbons utilised comprise at least 10, preferably at least 12 and most preferably greater than 20 carbon atoms per molecule.

Other preferred mineral oil extenders include alkylcycloaliphatic compounds, low molecular weight polyisobutylenes, Phosphate esters, alkybenzenes including polyalkylbenzenes which are unreactive with the polymer.

Any suitable mixture of mineral oil fractions may be utilised as the extender in the present invention but high molecular weight extenders (e.g. >220) are particularly preferred. Examples include:— alkylcyclohexanes (molecular weight>220);

paraffinic hydrocarbons and mixtures thereof containing from 1 to 99%, preferably from 15 to 80% n-paraffinic and/or isoparaffinic hydrocarbons (linear branched paraffinic) and 1 to 99%, preferably 85 to 20% cyclic hydrocarbons (naphthenic) and a maximum of 3%, preferably a maximum of 1% aromatic carbon atoms. The cyclic paraffinic hydrocarbons (naphthenics) may contain cyclic and/or polycyclic hydrocarbons. Any suitable mixture of mineral oil fractions may be used, e.g. mixtures containing (i) 60 to 80% paraffinic and 20 to 40% naphthenic and a maximum of 1% aromatic carbon atoms;
(ii) 30-50%, preferably 35 to 45% naphthenic and 70 to 50% paraffinic and or isoparaffinic oils;
(iii) hydrocarbon fluids containing more than 60 wt. % naphthenics, at least 20 wt. % polycyclic naphthenics and an ASTM D-86 boiling point of greater than 235° C.;
(iv) hydrocarbon fluid having greater than 40 parts by weight naphthenic hydrocarbons and less than 60 parts by weight paraffinic and/or isoparaffinic hydrocarbons based on 100 parts by weight of hydrocarbons.

Preferably the mineral oil based extender or mixture thereof comprises at least one of the following parameters:—

(i) a molecular weight of greater than 150, most preferably greater than 200;
(ii) an initial boiling point equal to or greater than 230° C. (according to ASTM D 86).
(iii) a viscosity density constant value of less than or equal to 0.9; (according to ASTM 2501)
(iv) an average of at least 12 carbon atoms per molecule, most preferably 12 to 30 carbon atoms per molecule;
(v) an aniline point equal to or greater than 70° C., most preferably the aniline point is from 80 to 110° C. (according to ASTM D 611);
(vi) a naphthenic content of from 20 to 70% by weight of the extender and a mineral oil based extender has a paraffinic content of from 30 to 80% by weight of the extender according to ASTM D 3238);
(vii) a pour point of from −50 to 60° C. (according to ASTM D 97);
(viii) a kinematic viscosity of from 1 to 20 cSt at 40° C. (according to ASTM D 445)
(ix) a specific gravity of from 0.7 to 1.1 (according to ASTM D1298);
(x) a refractive index of from 1.1 to 1.8.at 20° C. (according to ASTM D 1218)
(xi) a density at 15° C. of greater than 700 kg/m³ (according to ASTM D4052) and/or
(xii) a flash point of greater than 100° C., more preferably greater than 110° C. (according to ASTM D 93)
(xiii) a saybolt colour of at least +30 (according to ASTM D 156)
(xiv) a water content of less than or equal to 250 ppm
(xv) a Sulphur content of less than 2.5 ppm (according to ASTM D 4927)

Other organic extenders may include for the sake of example, fatty acids and fatty acid esters, alkylbenzene compounds suitable for use include heavy alkylate alkylbenzene or an alkylcycloaliphatic compound. Examples of alkyl substituted aryl compounds useful as extenders and/or plasticisers are compounds which have aryl groups, especially benzene substituted by alkyl and possibly other substituents, and a molecular weight of at least 200.

The alkylbenzene compounds suitable for use include heavy alkylate alkylbenzene or an alkylcycloaliphatic compound. Examples of alkyl substituted aryl compounds useful as extenders and/or plasticisers are compounds which have aryl groups, especially benzene substituted by alkyl and possibly other substituents, and a molecular weight of at least 200. Examples of such extenders are described in U.S. Pat. No. 4,312,801, the content of which is incorporated herein by reference. These compounds can be represented by general formula (2), (3), (4) and (5):—

(2)

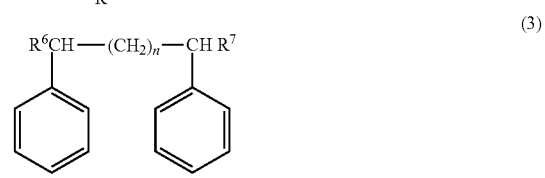

(3)

(4)

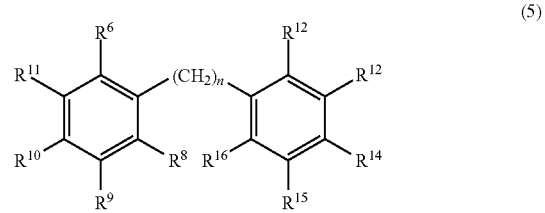

(5)

where $R^6$ is an alkyl chain of from 1 to 30 carbon atoms, each of $R^7$ through to $R^{16}$ is independently selected from hydrogen, alkyl, alkenyl, alkynyl, halogen, haloalkyl, nitrile, amine, amide, an ether such as an alkyl ether or an ester such as an alkyl ester group, and n is an integer of from 1 to 25.

Of these formula (2) where each of $R^7$, $R^8$, $R^9$, $R^{10}$ and $R^{11}$ is hydrogen and $R^6$ is a $C_{10}$-$C_{13}$ alkyl group. A particularly useful source of such compounds are the so-called "heavy alkylates", which are recoverable from oil refineries after oil distillation. Generally distillation takes place at temperatures in the range of from 230 to 330° C., and the heavy alkylates are present in the fraction remaining after the lighter fractions have been distilled off.

Examples of alkylcycloaliphatic compounds are substituted cyclohexanes with a molecular weight in excess of 220. Examples of such compounds are described in EP 0842974, the content of which is incorporated herein by reference. Such compounds may be represented by general formula (6).

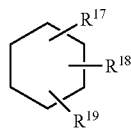

(6)

where $R^{17}$ is a straight or branched alkyl group of from 1 to 25 carbon atoms, and $R^{18}$ and $R^{19}$ are independently selected from hydrogen or a $C_{1-25}$ straight or branched chain alkyl group.

Alternatively the inert fluid may comprise may comprise a suitable non-mineral based natural oil or a mixture thereof, i.e. those derived from animals, seeds and nuts and not from mineral oils (i.e. not from petroleum or petroleum based oils) such as for example almond oil, avocado oil, beef tallow, borrage oil, butterfat, canola oil, cardanol, cashew nut oil, cashew nutshell liquid, castor oil, citrus seed oil, cocoa butter, coconut oil, cod liver oil, corn oil, cottonseed oil, cuphea oil, evening primrose oil, hemp oil, jojoba oil, lard, linseed oil, macadamia oil, menhaden oil, oat oil, olive oil, palm kernel oil, palm oil peanut oil, poppy seed oil, rapeseed oil, rice bran oil, safflower oil, safflower oil (high oleic), sesame oil, soybean oil, sunflower oil, sunflower oil (high oleic), tall oil, tea tree oil, turkey red oil, walnut oil perilla oil, dehydrated castor oils, apricot oil, pine nut oil, kukui nut oil, amazon nut oil almond oil, babasu oil, argan oil, black cumin oil, bearberry oil, calophyllum oil, camelina oil, carrot oil, carthamus oil, cucurbita oil, daisy oil, grape seed oil, foraha oil, jojoba oil, queensland oil, onoethera oil, ricinus oil, tamanu oil, tucuma oil, fish oils such as pilchard, sardine and herring oils. The extender may alternatively comprise mixtures of the above and/or derivatives of one or more of the above.

A wide variety of natural oil derivates are available. These include transesterified natural vegetable oils, boiled natural oils such as boiled linseed oil, blown natural oils and stand natural oils. An example of a suitable transesterified natural vegetable oil is known as biodiesel oil, the transesterification product produced by reacting mechanically extracted natural vegetable oils from seeds, such as rape, with methanol in the presence of a sodium hydroxide or potassium hydroxide catalyst to produce a range of esters dependent on the feed utilised. Examples might include for example methyloleate $(CH_3(CH_2)_7CH=CH(CH_2)_7CO_2CH_3)$.

Stand natural oils which are also known as thermally polymerised or heat polymerised oils and are produced at elevated temperatures in the absence of air. The oil polymerises by cross-linking across the double bonds which are naturally present in the oil. The bonds are of the carbon-carbon type. Stand oils are pale coloured and low in acidity. They can be produced with a wider range of viscosities than blown oils and are more stable in viscosity. In general, stand oils are produced from linseed oil and soya bean oil but can also be manufactured based on other oils. Stand oils are widely used in the surface coatings industry.

Blown oils which are also known as oxidised, thickened and oxidatively polymerised oils and are produced at elevated temperatures by blowing air through the oil. Again the oil polymerises by cross-linking across the double bonds but in this case there are oxygen molecules incorporated into the cross-linking bond. Peroxide, hydroperoxide and hydroxyl groups are also present. Blown oils may be produced from a wider range of oils than stand oils. In general, blown oils are darker in colour and have a higher acidity when compared to stand oils. Because of the wide range of raw materials used, blown oils find uses in many diverse industries, for example blown linseed oils are used in the surface coatings industry and blown rapeseed oils are often used in lubricants.

The amount of inert fluid which may be included in the composition will depend upon factors such as the purpose to which the composition is to be put, the molecular weight of the inert fluid(s) concerned etc. In general however, the higher the molecular weight of the inert fluids(s), the less will be tolerated in the composition but such high molecular weight inert fluids have the added advantage of lower volatility. Typical compositions will contain up to 70% w/w inert fluids(s). More suitable polymer products comprise from 5-60% w/w of inert fluid(s).

Such polysiloxane containing polymers as prepared in step (i) of the process in accordance with the present invention may be made by a variety of routes with the polymers produced being end-capped with compounds which will provide the required terminal groupings on the polymer and provided the polymer or its precursors and/or intermediates is/are diluted in the inert fluid described above during the polymerisation process. Preferred routes to the preparation of said polymers include
(i) polycondensation
(ii) ring opening/equilibrium
(iii) polyaddition
(iv) chain extension (i) Polycondensation (i.e. the polymerisation of multiple monomers and/or oligomers with the elimination of low molecular weight by-product(s) such as water, ammonia or methanol etc.). Any suitable polycondensation reaction pathway may be utilised.

The sort of reaction envisaged between the condensable end groups of the starting materials are most preferably generally linked to the interaction of compounds having hydroxyl and/or hydrolysable end groups which can interact with the release of e.g. water or methanol or the like. However, the following list indicates other interactions which might be considered for the cure process of the composition in accordance with the present invention:—

1) the condensation of organohalosilyl groups with an organoalkoxysilyl groups,
2) the condensation of organohalosilyl groups with organoacyloxysilyl groups,
3) the condensation of organohalosilyl groups with organosilanols,
4) the condensation of organohalosilyl groups with silanolates,
5) the condensation of organo-hydrosilyl groups with organosilanol groups
6) the condensation of organoalkoxysilyl groups with organoacyloxysilyl groups 7) the condensation of organoalkoxysilyl groups with organosilanol groups,
8) the condensation of organoaminosilyl groups with organosilanols,
9) the condensation of organoacyloxysilyl groups silanolate groups
10) the condensation of organoacyloxysilyl groups with organosilanols,
11) the condensation of organooximosilyl groups with organosilanol groups
12) the condensation of organoenoxysilyl groups with organosilanols,
13) The condensation of a siloxane compound comprising one or more hydrosilane functional groups with a siloxane compounds containing at least one alkoxysilane functional group, generating hydrocarbon by-products.

Most preferably the condensation reaction which occurs between monomers/oligomers and intermediates with hydroxyl and/or alkoxy end-groups thereby producing water or alcohols as a by-product.

A preferred method for the polymerisation process is the polymerisation of straight chain precursors and/or branched organopolysiloxanes of formula (1) including for example

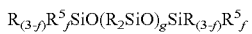

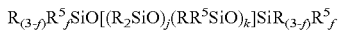

Where R is as previously defined, $R^5$ is —OH or an alkoxy group having from 1 to 6 carbon atoms, preferably a methoxy or ethoxy group, f is 0 or 1, preferably 1, g is an integer from 2 to 100, h is from 2 to 100, j is an integer from 1 to 100 and k is an integer between 1 to 100. Some branching may occur with the presence of other groups in the polymeric chain but preferably this is kept to a minimum.

The above starting materials preferably have a viscosity of between 10 mPa·s and 5000 mPa·s at 25° C.

Many of the above processes require the presence of catalyst. Any suitable polycondensation catalyst may be utilised including tin, lead, antimony, iron, cadmium, barium, manganese, zinc, chromium, cobalt, nickel, titanium, aluminium, gallium or germanium and zirconium based catalysts such as organic tin metal catalysts and 2-ethylhexoates of iron, cobalt, manganese, lead and zinc may alternatively be used.

Tin catalysts may include as triethyltin tartrate, tin octoate, tin oleate, tin naphthate, butyltintri-2-ethylhexoate, tinbutyrate, carbomethoxyphenyl tin trisuberate, isobutyltintriceroate, and diorganotin salts especially diorganotin dicarboxylate compounds such as dibutyltin dilaurate, dimethyltin dibutyrate, dibutyltin dimethoxide, dibutyltin diacetate, dimethyltin bisneodecanoate Dibutyltin dibenzoate, stannous octoate, dimethyltin dineodeconoate, dibutyltin dioctoate. Dibutyltin dilaurate, dibutyltin diacetate are particularly preferred.

Titanate catalysts may comprise a compound according to the general formula Ti[OR$^{20}$]$_4$ and Zr[OR$^{20}$]$_4$ respectively where each R$^{20}$ may be the same or different and represents a monovalent, primary, secondary or tertiary aliphatic hydrocarbon group which may be linear or branched containing from 1 to 10 carbon atoms. Optionally the titanate may contain partially unsaturated groups. However, preferred examples of R$^{20}$ include but are not restricted to methyl, ethyl, propyl, isopropyl, butyl, tertiary butyl and a branched secondary alkyl group such as 2,4-dimethyl-3-pentyl. Preferably, when each R$^{20}$ is the same, R$^{20}$ is an isopropyl, branched secondary alkyl group or a tertiary alkyl group, in particular, tertiary butyl. Examples include tetrabutyltitanate, tetraisopropyltitanate, or chelated titanates or zirconates such as for example diisopropyl bis(acetylacetonyl)titanate, diisopropyl bis(ethylacetoacetonyl)titanate, diisopropoxytitanium Bis(Ethylacetoacetate) and the like. Further examples of suitable catalysts are described in EP1254192 and/or WO200149774 the contents of which are incorporated herein by reference. The amount of catalyst used depends on the cure system being used but typically is from 0.01 to 3% by weight of the total composition.

Other condensation catalysts which may be used, protic acids, Lewis acids, organic and inorganic bases, metal salts and organometallic complexes. Lewis acid catalysts. (a "Lewis acid" is any substance that will take up an electron pair to form a covalent bond). suitable for the polymerisation in the present invention include, for example, boron trifluoride FeCl$_3$, AlCl$_3$, ZnCl$_2$, and ZnBr$_2$.

More preferred are condensation specific catalysts such as acidic condensation catalysts of the formula R$^{21}$SO$_3$H in which R$^{21}$ represents an alkyl group preferably having from 6 to 18 carbon atoms such as for example a hexyl or dodecyl group, an aryl group such as a phenyl group or an alkaryl group such as dinonyl- or didoecyl-naphthyl. Water may optionally be added. Preferably R$^{21}$ is an alkaryl group having an alkyl group having from 6 to 18 carbon atoms such as dodecylbenzenesulphonic acid (DBSA). Other condensation specific catalysts include n-hexylamine, tetramethylguanidine, carboxylates of rubidium or caesium, hydroxides of magnesium, calcium or strontium and other catalysts as are mentioned in the art, e.g. in GB895091, GB918823 and EP 0382365. Also preferred are catalysts based on phosphonitrile chloride, for example those prepared according to U.S. Pat. No. 3,839,388, U.S. Pat. No. 4,564,693 or EP215 470 and phosphonitrile halide ion based catalysts, as described in GB2252975, having the general formula $[X(PX_2=N)_pPX_3]^+[M^2X_{(m-n+1)}R^{III}_m]^-$, wherein X denotes a halogen atom, $M^2$ is an element having an electronegativity of from 1.0 to 2.0 according to Pauling's scale, $R^{III}$ is an alkyl group having up to 12 carbon atoms, p has a value of from 1 to 6, m is the valence or oxidation state of $M^2$ and n has a value of from 0 to m−1.

Alternatively the catalyst may comprise an oxygen-containing chlorophosphazene containing organosilicon radicals having the following general formula:—

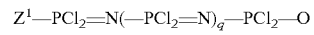

in which
Z$^1$ represents an organosilicon radical bonded to phosphorus via oxygen, a chlorine atom of the hydroxyl group and
q represents 0 or an integer from 1 to 8. The catalyst may also comprise condensation products of the above and/or tautomers thereof (the catalyst exists in a tautomeric form when Z$^1$ is a hydroxyl group).

A further alternative catalyst which might be used as the catalyst in the present invention is any suitable compound providing a source of anions comprising at least one quadrisubstituted boron atom and protons capable of interaction with at least one silanol group as defined in WO 01/79330.

The activity of the catalyst is preferably quenched by using a neutralizing agent which reacts with the catalyst to render it non-active. Typically in the case of the acid type condensation catalysts the neutralising agent is a suitable base such as an amine such as a mono/di and trialkanolamines for example monoethanolamine (MEA) and triethanolamine (TEA). In the case of systems using a DBSA catalyst alternative quenching means include aluminasilicate zeolite materials that were found to absorb DBSA and leave a stable polymer. In most cases catalyst residues remain in the polymer product or where appropriate may be removed by filtration or alternative methods. In the case of phosphazene based catalysts when the desired viscosity has been reached, the viscosity of the organosilicon compound obtained in the process can be kept constant by a procedure in which the catalyst used, or a reaction product which has been formed from this catalyst by reaction with organosilicon compound to be subjected to condensation and/or equilibration and likewise promotes the condensation and/or equilibration of organosilicon compounds, is inhibited or deactivated by addition of inhibitors or deactivators which have been employed to date in connection with phosphazenes, for example, triisononylamine, n-butyllithium, lithium siloxanolate, hexamethylcyclotrisilazane, hexamethyldisilazane and magnesium oxide.

Where appropriate any suitable end-blocking agent, which halts the polymerization reaction and thereby limits the average molecular weight, may be used to introduce the appropriate end-groups in polymer (a).

(II) Equilibration/Ring Opening

The starting material for equilibration polymerisation processes such as ring-opening polymerisation is a cyclosiloxane (also known as a cyclic siloxane). Cyclic siloxanes which are useful are well known and commercially available materials. They have the general formula $(R^{22}SiO)_r$, wherein each $R^{22}$ is selected from an alkyl group, an alkenyl group, an aryl group or an aralkyl group and r denotes an integer with a value of from 3 to 12. $R^{22}$ can contain substitution, e.g. by halogen such as fluorine or chlorine. The alkyl group can be, for example, methyl, ethyl, n-propyl, trifluoropropyl, n-butyl, sec-butyl, and tert-butyl. The alkenyl group can be, for example, vinyl, allyl, propenyl, and butenyl. The aryl and aralkyl groups can be, for example, phenyl, tolyl, and benzoyl. The preferred groups are methyl, ethyl, phenyl, vinyl, and trifluoropropyl. Preferably at least 80% of all $R^{22}$ groups are methyl or phenyl groups, most preferably methyl. Preferably the average value of r is from 3 to 6. Examples of suitable cyclic siloxanes are octamethylcyclotetrasiloxane, hexamethylcyclotrisiloxane, decamethylcyclopentasiloxane, cyclopenta(methylvinyl)siloxane, cyclotetra(phenylmethyl)siloxane, cyclopentamethylhydrosiloxane and mixtures thereof. One particularly suitable commercially available material is a mixture of comprising octamethylcyclotetrasiloxane and decamethylcyclopentasiloxane. Typically moisture is present in the monomers. The water present acts as an end-blocker by forming OH end groups on the polymers thereby preventing further polymerisation.

Any suitable catalyst may be used. These include alkali metal hydroxides such as lithium hydroxide, sodium hydroxide, potassium hydroxide or caesium hydroxide, alkali metal alkoxides or complexes of alkali metal hydroxides and an alcohol, alkali metal silanolates such as potassium silanolate caesium silanolate, sodium silanolate and lithium silanolate or trimethylpotassium silanolate. Other catalysts which might be utilised include the catalyst derived by the reaction of a tetra-alkyl ammonium hydroxide and a siloxane tetramer and the boron based catalysts as hereinbefore described.

Catalysts which are most preferred for equilibrium type reactions however are phosphonitrile halides, phosphazene acids and phosphazene bases as hereinbefore described.

Where required the polymer obtained may be end-blocked as a means of regulating the molecular weight of the polymer and/or to add functionality. Whilst this end-blocking function can be achieved by water as discussed above, other suitable end-blocking agents include silanes having one group capable of reacting with the terminal groups of the resulting polymeric constituent prepared in the diluted polymer to produce the required end-groups for polymer (a).

(III) Polyaddition

For the sake of this specification a "polyaddition" or "addition polymerisation" process is a polymerisation process whereby unlike in a condensation reaction no by-products such as water or alcohols are generated from the monomeric and oligomeric co-reactants during polymerisation. A preferred addition polymerisation route is a hydrosilylation reaction between an unsaturated organic group e.g. an alkenyl or alkynyl group and an Si—H group in the presence of a suitable catalyst. In this route suitable silanes may be utilised as well as siloxane containing monomers and/or oligomers.

Typically the polyaddition route is utilised to form block copolymers by reacting a) (i) an organopolysiloxane or (ii) a silane with:—
b) one or more organopolysiloxane polymer(s)
via an addition reaction pathway in the presence of the extender and/or plasticiser, and a suitable catalyst and optionally an end-blocking agent; and
where required quenching the polymerisation process.

The organopolysiloxane or silane (a) is selected from a silane (a) (ii) containing at least one group capable of undergoing addition type reactions and an organopolysiloxane monomer (a) (i) containing groups capable of undergoing addition type reactions. The organopolysiloxane or silane (a) must contain substituents such that it is capable of undergoing an appropriate addition reaction with polymer (b). The preferred addition reaction is a hydrosilylation reaction between an unsaturated group and an Si—H group.

Preferably silane (a) (ii) has at least 1 and preferably 2 groups capable of undergoing addition type reactions with (b). When the addition reaction is a hydrosilylation reaction the silane may contain an unsaturated constituent but preferably contains at least one Si—H group. Most preferably each silane contains one or more Si—H groups. In addition to the one or more Si—H groups, preferred silanes may include for example an alkyl group, an alkoxy group, an acyloxy group, a ketoximato group, an amino group, an amido group, an acid amido group, an aminoxy group, a mercapto group, an alkenyloxy group and the like. Among these, alkoxy, acyloxy, ketoximato, amino, amido, aminoxy, mercapto and alkenyloxy groups are preferred. Practical examples of the silicon hydride are halosilane tri-chlorosilane, methyl dichlorosilane, dimethyl chlorosilane, and phenyl dichlorosilane; alkoxy silanes, such as tri-methyoxy silane, tri-ethoxy silane, methyl di-ethoxy silane, methyl di-methoxy silane and phenyl-di-methoxy silane; acyloxy silanes, such as methyl di-acetoxy silane and phenyl diacetoxy silane; and ketoximato silanes, such as bis-(dimethylketoximate)-methyl silane and bis-(cyclohexyl ketoximate) methyl silane. Among them, halosilanes and alkoxyl silanes are preferred. Particularly preferred silanes include for example methyl dimethoxy silane (H—Si(—CH$_3$)(—OCH$_3$)$_2$).

It will be appreciated that the addition reaction between silane (a) (ii) and (b) results in a polymer chain extension process or as a means of end—blocking a polymer with pre-required end groups, in which case the extender may be added in combination with silane (a) (ii), i.e. immediately prior to the addition reaction or may be present during the polymerisation of polymer (b) and as such silane (a) (ii) is added to an extended polymer (b) which has been polymerised in the presence of the extender.

Organopolysiloxane monomer (a) (i) is preferably in the form of a straight chain and/or branched organopolysiloxane comprising units of formula (1a)

$$R'_a SiO_{4-a'/2} \tag{1a}$$

wherein each R' may be the same or different and denotes a hydrocarbon group having from 1 to 18 carbon atoms, a substituted hydrocarbon group having from 1 to 18 carbon atoms or a hydrocarbonoxy group having up to 18 carbon atoms and a' has, on average, a value of from 1 to 3, preferably 1.8 to 2.2. Preferably each R' is the same or different and is exemplified by, but not limited to hydrogen, alkyl groups such as methyl, ethyl, propyl, butyl, pentyl, hexyl, heptyl, octyl, undecyl, and octadecyl; cycloalkyl such as cyclohexyl; aryl such as phenyl, tolyl, xylyl, benzyl, and 2-phenylethyl; and halogenated hydrocarbon groups such as 3,3,3-trifluoropropyl, 3-chloropropyl, and dichlorophenyl. Some R' groups may be hydrogen groups. Preferably the polydiorganosiloxanes are polydialkylsiloxanes, most preferably polydimethylsiloxanes. When (a) is an organopolysiloxane monomer, said organopolysiloxane monomer must have at least one group which is reactable with at least two groups, typically the terminal groups, of (b) via an addition reaction process. Preferably organopolysiloxane (a) (i) comprises at least one Si—H per molecule, preferably at least two Si—H groups per molecule. Preferably organopolysiloxane (a) (i) is end-blocked with a siloxane group of the formula $H(R")_2 SiO_{1/2}$, wherein each R" is a hydrocarbon or substituted hydrocarbon group, most preferably an alkyl group. Preferably organopolysiloxane (a) (i) has a viscosity of between 10 mPa·s and 5000 mPa·s at 25° C.

Organopolysiloxane polymer (b) is preferably a straight chain and/or branched organopolysiloxane comprising units of formula (1b)

$$R'''_a SiO_{4-a'/2} \tag{1b}$$

wherein each R''' may be the same or different and denotes a hydrocarbon group having from 1 to 18 carbon atoms, a substituted hydrocarbon group having from 1 to 18 carbon atoms or a hydrocarbonoxy group having up to 18 carbon atoms and a' is as previously described. Preferably no R''' groups may be hydrogen groups. Preferably each R''' is the same or different and are exemplified by, but not limited to alkyl groups such as methyl, ethyl, propyl, butyl, pentyl, hexyl, heptyl, octyl, undecyl, and octadecyl; cycloalkyl such as cyclohexyl; aryl such as phenyl, tolyl, xylyl, benzyl, and 2-phenylethyl; and halogenated hydrocarbon groups such as 3,3,3-trifluoropropyl, 3-chloropropyl, and dichlorophenyl.

Organopolysiloxane polymer (b) may comprise any suitable organopolysiloxane polymeric backbone but is preferably linear or branched, and comprises at least one, preferably at least two substituent groups which will react with the aforementioned groups in the organopolysiloxane or silane (a) via an addition reaction pathway. Preferably the or each addition reactive substituent group of polymer (b) is a terminal group. When the organopolysiloxane or silane (a) comprises at least one Si—H group, the preferred substituent groups on organopolysiloxane polymer (b), which are designed to interact with the Si—H groups, are preferably unsaturated groups (e.g. alkenyl terminated e.g. ethenyl terminated, propenyl terminated, allyl terminated ($CH_2=CHCH_2$—)) or terminated with acrylic or alkylacrylic such as $CH_2=C(CH_3)$—$CH_2$— groups Representative, non-limiting examples of the alkenyl groups are shown by the following structures; $H_2C=CH$—, $H_2C=CHCH_2$—, $H_2C=C(CH_3)CH_2$—, $H_2C=CHCH_2CH_2$—, $H_2C=CHCH_2CH_2CH_2$—, and $H_2C=CHCH_2CH_2CH_2CH_2$—. Representative, non-limiting examples of alkynyl groups are shown by the following structures; $HC\equiv C$—, $HC\equiv CCH_2$—, $HC\equiv C(CH_3)$—, $HC\equiv CC(CH_3)_2$—, $HC\equiv CC(CH_3)_2CH_2$— Alternatively, the unsaturated organic group can be an organofunctional hydrocarbon such as an acrylate, methacrylate and the like such as alkenyl an/or alkynyl groups. Alkenyl groups are particularly preferred.

In cases where the organopolysiloxane or silane (a) comprises only one addition reactable group and (b) comprises two addition reactable groups which will react with the organopolysiloxane or silane (a), the resulting product will be an "ABA" type polymeric product. Whereas when both the organopolysiloxane or silane (a) comprises two addition reactable groups and (b) comprises two addition reactable groups which will react with the organopolysiloxane or silane (a) interaction between the two components would lead to (AB)n block copolymers in which the length of the polymer is largely determined by the relative amounts of the two constituents.

It will also be appreciated that this hydrosilylation route may be utilised to prepare silicone-organic copolymers by using an organopolysiloxane polymer which contains organic groups in the polymer backbone or by replacing organopolysiloxane polymer (b) with, for example alkenyl terminated polyethers Hence linear non-hydrolysable (AB)n block copolymers in accordance with the present invention of this invention can be prepared by catalyzed hydrosilylation of alkenyl terminated polyethers with SiH-terminated dialkylsiloxane fluids. The resulting copolymer being a combination of polyoxyalkylene blocks linked through silicon to carbon to oxygen linkages (i.e. a propyleneoxy group) and the endblocking groups being selected from the group consisting of allyl, propenyl and/or hydrogen (dialkyl) siloxy groups (dependent on the relative amounts of the constituents which are present).

When the addition reaction chosen is a hydrosilylation reaction, any suitable hydrosilylation catalyst may be utilised. Such hydrosilylation catalysts are illustrated by any metal-containing catalyst which facilitates the reaction of silicon-bonded hydrogen atoms of the SiH terminated organopolysiloxane with the unsaturated hydrocarbon group on the polyoxyethylene. The metals are illustrated by ruthenium, rhodium, palladium, osmium, iridium, or platinum.

Hydrosilylation catalysts are illustrated by the following; chloroplatinic acid, alcohol modified chloroplatinic acids, olefin complexes of chloroplatinic acid, complexes of chloroplatinic acid and divinyltetramethyldisiloxane, fine platinum particles adsorbed on carbon carriers, platinum supported on metal oxide carriers such as $Pt(Al_2O_3)$, platinum black, platinum acetylacetonate, platinum(divinyltetramethyldisiloxane), platinous halides exemplified by $PtCl_2$, $PtCl_4$, $Pt(CN)_2$, complexes of platinous halides with unsaturated compounds exemplified by ethylene, propylene, and organovinylsiloxanes, styrene hexamethyldiplatinum. Such noble metal catalysts are described in U.S. Pat. No. 3,923, 705, incorporated herein by reference to show platinum catalysts. One preferred platinum catalyst is Karstedt's catalyst, which is described in Karstedt's U.S. Pat. Nos. 3,715, 334 and 3,814,730, incorporated herein by reference. Karstedt's catalyst is a platinum divinyl tetramethyl disiloxane complex typically containing one weight percent of platinum in a solvent such as toluene. Another preferred platinum catalyst is a reaction product of chloroplatinic acid and an organosilicon compound containing terminal aliphatic unsaturation. It is described in U.S. Pat. No. 3,419,593, incorporated herein by reference. Most preferred as the catalyst is a neutralized complex of platinous chloride and divinyl tetramethyl disiloxane, for example as described in U.S. Pat. No. 5,175,325.

Ruthenium catalysts such as $RhCl_3(Bu_2S)_3$ and ruthenium carbonyl compounds such as ruthenium 1,1,1-trifluoroacetylacetonate, ruthenium acetylacetonate and triruthinium dodecacarbonyl or a ruthenium 1,3-ketoenolate may alternatively be used.

Other hydrosilylation catalysts suitable for use in the present invention include for example rhodium catalysts such as $[Rh(O_2CCH_3)_2]_2$, $Rh(O_2CCH_3)_3$, $Rh_2(C_8H_{15}O_2)_4$, $Rh(C_5H_7O_2)_3$, $Rh(C_5H_7O_2)(CO)_2$, $Rh(CO)[Ph_3P]$ $(C_5H_7O_2)$, $RhX^4_3[(R^3)_2S]_3$, $(R^2_3P)_2Rh(CO)X^4$, $(R^2_3P)_2Rh(CO)H$, $Rh_2X^4_2Y^4_4$, $H_aRh_b\text{olefin}_cCl_d$, $Rh(O(CO)R^3)_{3-n}(OH)_n$ where $X^4$ is hydrogen, chlorine, bromine or iodine, $Y^4$ is an alkyl group, such as methyl or ethyl, CO, $C_8H_{14}$ or 0.5 $C_8H_{12}$, $R^3$ is an alkyl radical, cycloalkyl radical or aryl radical and $R^2$ is an alkyl radical an aryl radical or an oxygen substituted radical, a is 0 or 1, b is 1 or 2, c is a whole number from 1 to 4 inclusive and d is 2, 3 or 4, n is 0 or 1. Any suitable iridium catalysts such as $Ir(OOCCH_3)_3$, $Ir(C_5H_7O_2)_3$, $[Ir(Z^2)(En)_2]_2$, or $(Ir(Z^2)(Dien)]_2$, where $Z^2$ is chlorine, bromine, iodine, or alkoxy, En is an olefin and Dien is cyclooctadiene may also be used.

The hydrosilylation catalyst may be added to the present composition in an amount equivalent to as little as 0.001 part by weight of elemental platinum group metal, per one million parts (ppm) of the composition. Preferably, the concentration of the hydrosilylation catalyst in the composition is that capable of providing the equivalent of at least 1 part per million of elemental platinum group metal. A catalyst concentration providing the equivalent of about 3-50 parts per million of elemental platinum group metal is generally the amount preferred.

Typically when (a) has at least two Si—H groups, typically, the process is carried out using approximately a 1:1 molar ratio of (a) to (b). However, useful materials may also be prepared by carrying out the process with an excess of either (a) or (b) but this would be considered a less efficient use of the materials. Typically, the material containing the unsaturation (b) is used in slight excess to ensure all the Si—H is consumed in the reaction. As polymer (b) used in the present invention is preferably terminated with unsaturated end-groups, end-blocking agents are not typically required when making the polymer via this route. However, they may be utilised if required.

Optionally when a hydrosilylation route is utilised for polymerisation a suitable hydrosilylation catalyst inhibitor may be required. Any suitable platinum group type inhibitor may be used. One useful type of platinum catalyst inhibitor is described in U.S. Pat. No. 3,445,420, which is hereby incorporated by reference to show certain acetylenic inhibitors and their use. A preferred class of acetylenic inhibitors are the acetylenic alcohols; especially 2-methyl-3-butyn-2-ol and/or 1-ethynyl-2-cyclohexanol which suppress the activity of a platinum-based catalyst at 25° C. A second type of platinum catalyst inhibitor is described in U.S. Pat. No. 3,989,667, which is hereby incorporated by reference to show certain olefinic siloxanes, their preparation and their use as platinum catalyst inhibitors. A third type of platinum catalyst inhibitor includes polymethylvinylcyclosiloxanes having three to six methylvinylsiloxane units per molecule.

Compositions containing these hydrosilylation catalysts typically require heating at temperatures of 70° C. or above to cure at a practical rate, particularly if an inhibitor is used. Room temperature cure is typically accomplished with such systems by use of a two-part system in which the crosslinker and inhibitor are in one of the two parts and the platinum is in the other part. The amount of platinum is increased to allow for curing at room temperature. The optimum concentration of platinum catalyst inhibitor is that which will provide the desired storage stability or pot life at ambient temperature without excessively prolonging the time interval required to cure the present compositions at elevated temperatures. This amount will vary widely and will depend upon the particular inhibitor that is used. Inhibitor concentrations as low as one mole of inhibitor per mole of platinum will in some instances yield a desirable level of storage stability and a sufficiently short curing period at temperatures above about 70° C. In other cases, inhibitor concentrations of up to 10, 50, 100, 500 or more moles per mole of platinum may be needed. The optimum concentration for a particular inhibitor in a given composition can be determined by routine experimentation.

Additional components can be added to the hydrosilylation reaction which are known to enhance such reactions. These components include salts such as sodium acetate which have a buffering effect in combination with platinum based catalysts.

For this type of polymerisation the amount of hydrosilylation catalyst used is not narrowly limited as long as there is a sufficient amount to accelerate a reaction between
(a) (i) an organopolysiloxane or (ii) a silane the chosen of which must contain at least one and preferably at least two Si—H groups with
(b) one or more organopolysiloxane polymer(s) or an alternative therefore such as a polyoxyethylene having an unsaturated hydrocarbon group at each molecular terminal at room temperature or at temperatures above room temperature. The actual amount of this catalyst will depend on the particular catalyst utilized and is not easily predictable. However, for platinum-containing catalysts the amount can be as low as one weight part of platinum for every one million weight parts of components (a) and (b). The catalyst can be added at an amount 10 to 120 weight parts per one million parts of components (a) and (b), but is typically added in an amount from 10 to 60 weight parts per one million parts of (a) and (b).

Where appropriate, polymers obtained via a hydrosilylation route can also be cured and/or crosslinked by a hydrosilylation reaction catalyst in combination with an organohydrogensiloxane as the curing agent providing each polymer molecule produced contains at least two unsaturated groups suitable for cross-linking with the organohydrogensiloxane. To effect curing of the present composition, the organohydrogensiloxane must contain more than two silicon bonded hydrogen atoms per molecule. The organohydrogensiloxane can contain, for example, from about 4-20 silicon atoms per molecule, and have a viscosity of up to about 10 Pa·s at 25° C. The silicon-bonded organic groups present in the organohydrogensiloxane can include substituted and unsubstituted alkyl groups of 1-4 carbon atoms that are otherwise free of ethylenic or acetylenic unsaturation.

(IV) Chain Extension

In this case rather than adding chain extender into a final pre-prepared polymer composition the extender is mixed into the polymer during a chain extension polymerisation step. Typically the polymeric starting material is an organopolysiloxane having end groups suitable for interaction with the chosen chain extending materials. Typically the polymer end groups are either hydrolysable or suitable for addition reaction (typically hydrosilylation) and the chain extending material is chosen on the basis of having suitable reactive groups which will chain extend the polymer. Preferred chain extending materials for chain extending polymers having hydroxyl and/or hydrolysable end groups are as hereinbefore described.

For pre-formed polymers with alkenyl or Si—H groups (typically end groups) suitable for addition reactions via a hydrosilylation route the chain extender will contain two groups which will undergo an addition reaction with the respective addition reactive groups on the chosen polymer. Such chain extenders may include for example:—
A silane comprising two alkenyl groups, a dihydrosilane, a polydialkylsiloxane having a degree of polymerisation of from 2 to 25 and at least one Si-alkenyl bond per terminal group, A polydialkylsiloxane having a degree of polymerisation of from 2 to 25 and at least one Si—H bond per terminal group and wherein each alkyl group independently comprises from 1 to 6 carbon atoms;
organosilicon compounds with the general formula

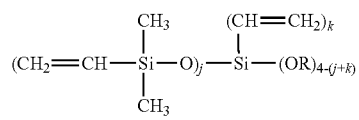

in which R is as hereinbefore described, j is 1, 2, or 3, k is 0 or 1, and j+k is 2 or 3. exemplified by compounds with the following formulas, (ViMe$_2$SiO)$_2$SiVi(OMe)$_1$
(ViMe$_2$SiO)$_1$SiVi(OMe)$_2$, (ViMe$_2$SiO)$_2$SiVi(OEt)$_1$, (ViMe$_2$SiO)$_1$SiVi(OEt)$_2$, (ViMe$_2$SiO)$_3$Si(OMe)$_1$, (ViMe$_2$SiO)$_2$Si(OMe)$_2$, (ViMe$_2$SiO)$_3$Si(OEt)$_1$ and (ViMe$_2$SiO)$_2$Si(OEt)$_2$
As used herein, Vi represents a vinyl group, Me represents a methyl group, and Et represents an ethyl group.

The catalyst used to catalyse the chain extension reaction is determined by the reaction to take place. When the reaction occurring is a condensation reaction any suitable condensation catalyst as hereinbefore described may be utilised. When the reaction occurring is a hydrosilylation reaction any suitable hydrosilylation catalyst as hereinbefore described may be utilised.

Where required the polymer contains hydrolysable terminal groups, end-blocking agents as described above in relation to condensation may be utilised to obtain appropriate terminal groups. Where required the polymer contains addition reactable terminal groups, end-blocking agents as described above in relation to polyaddition may be utilised to obtain appropriate terminal groups.

The process can be carried out either batchwise or continuously on any suitable mixers. In case of a polycondensation, generated water can either be removed by chemical drying using e.g. hydrolysable silanes like methyltrimethoxysilane or by physical separation using evaporation, coalescing or centrifuging techniques.

Chain extension may take place at any suitable temperature and pressure for the process concerned in batch or continuous modes of operation as preferred. Hence in the case of the phosphazene catalysed methods polymerisation may occur at temperatures of between 50° C. to 200° C., more preferably 80° C. to 160° C. Furthermore, in order to facilitate removal of the by-products formed during the condensation, for example, water, HCl or alcohol, the condensation and/or equilibration of the organosilicon compounds may be carried out at a pressure below 80 kPa. Alternative methods for the removal of condensation by-products include removal by chemical drying using e.g. hydrolysable silanes like methyltrimethoxysilane (where appropriate) or by physical separation using evaporation, coalescing or centrifuging techniques.

The process can be carried out either batchwise or continuously on any suitable mixers. In case of a polycondensation, generated water can either be removed by chemical drying using e.g. hydrolysable silanes like methyltrimethoxysilane or by physical separation using evaporation, coalescing or centrifuging techniques.

Preferably the viscosity of the mixture of the polymer and inert fluid prior to emulsifying is in the range of viscosity of 1000-100000 mPa·s at 25° C. and preferably the viscosity of the polymer in the emulsion is greater than 1 000 000 mPa·s at 25° C.

Any suitable surfactant or combination of surfactants may be utilised. The surfactant can in general be a non-ionic surfactant, a cationic surfactant, an anionic surfactant, or an amphoteric surfactant, although not all procedures for carrying out the process of the invention can be used with all surfactants. The amount of surfactant used will vary depending on the surfactant, but generally is up to about 30 wt. % based on the polydiorganosiloxane.

Examples of nonionic surfactants include condensates of ethylene oxide with long chain fatty alcohols or fatty acids such as a C$_{12-16}$ alcohol, condensates of ethylene oxide with an amine or an amide, condensation products of ethylene and propylene oxide, esters of glycerol, sucrose, sorbitol, fatty acid alkylol amides, sucrose esters, fluoro-surfactants, fatty amine oxides, polyoxyalkylene alkyl ethers such as polyethylene glycol long chain (12-14C) alkyl ether, polyoxyalkylene sorbitan ethers, polyoxyalkylene alkoxylate esters, polyoxyalkylene alkylphenol ethers, ethylene glycol propylene glycol copolymers and alkylpolysaccharides, for example materials of the structure $R^{24}$—O—$(R^{25}O)_s$-$(G)_t$ wherein $R^{24}$ represents a linear or branched alkyl group, a linear or branched alkenyl group or an alkylphenyl group, $R^{25}$ represent an alkylene group, G represents a reduced sugar, s denotes 0 or a positive integer and t represent a positive integer as described in U.S. Pat. No. 5,035,832. non ionic surfactants additionally include polymeric surfactants such as polyvinyl alcohol (PVA) and polyvinylmethylether.

Representative examples of suitable commercially available nonionic surfactants include polyoxyethylene fatty alcohols sold under the tradename BRIJ® by Uniqema (ICI Surfactants), Wilmington, Del. Some examples are BRIJ® 35 Liquid, an ethoxylated alcohol known as polyoxyethylene (23) lauryl ether, and BRIJ® 30, another ethoxylated alcohol known as polyoxyethylene (4) lauryl ether. Some additional nonionic surfactants include ethoxylated alcohols sold under the trademark TERGITOL® by The Dow Chemical Company, Midland, Mich. Some example are TERGITOL® TMN-6, an ethoxylated alcohol known as ethoxylated trimethylnonanol; and various of the ethoxylated alcohols, i.e., C$_{12}$-C$_{14}$ secondary alcohol ethoxylates, sold under the trademarks TERGITOL® 15-S-5; TERGITOL® 15-S-12, TERGITOL® 15-S-15, and TERGITOL® 15-S-40. Surfactants containing silicon atoms can also be used.

Examples of suitable amphoteric surfactants include imidazoline compounds, alkylaminoacid salts, and betaines. Specific examples include cocamidopropyl betaine; cocamidopropyl hydroxysulfate, cocobetaine, sodium cocoamidoacetate, cocodimethyl betaine, N-coco-3-aminobutyric acid and imidazolinium carboxyl compounds. Representative examples of suitable amphoteric surfactants include imidazoline compounds, alkylaminoacid salts, and betaines.

Examples of cationic surfactants include quaternary ammonium hydroxides such as octyl trimethyl ammonium hydroxide, dodecyl trimethyl ammonium hydroxide, hexadecyl trimethyl ammonium hydroxide, octyl dimethyl benzyl ammonium hydroxide, decyl dimethyl benzyl ammonium hydroxide, didodecyl dimethyl ammonium hydroxide, dioctadecyl dimethyl ammonium hydroxide, tallow trimethyl ammonium hydroxide and coco trimethyl ammonium hydroxide as well as corresponding salts of these materials, fatty amines and fatty acid amides and their derivatives, basic pyridinium compounds, quaternary ammonium bases of benzimidazolines and polypropanolpolyethanol amines. Other representative examples of suitable cationic surfactants include alkylamine salts, sulphonium salts, and phosphonium salts.

Examples of suitable anionic surfactants include alkyl sulphates such as lauryl sulphate, polymers such as acrylates/$C_{10-30}$ alkyl acrylate crosspolymer alkylbenzenesulfonic acids and salts such as hexylbenzenesulfonic acid, octylbenzenesulfonic acid, decylbenzenesulfonic acid, dodecylbenzenesulfonic acid, cetylbenzenesulfonic acid and myristylbenzenesulfonic acid; the sulphate esters of monoalkyl polyoxyethylene ethers; alkylnapthylsulfonic acid; alkali metal sulforecinates, sulfonated glyceryl esters of fatty acids such as sulfonated monoglycerides of coconut oil acids, salts of sulfonated monovalent alcohol esters, amides of amino sulfonic acids, sulfonated products of fatty acid nitriles, sulfonated aromatic hydrocarbons, condensation products of naphthalene sulfonic acids with formaldehyde, sodium octahydroanthracene sulfonate, alkali metal alkyl sulphates, ester sulphates, and alkarylsulfonates. Anionic surfactants include alkali metal soaps of higher fatty acids, alkylaryl sulphonates such as sodium dodecyl benzene sulphonate, long chain fatty alcohol sulphates, olefin sulphates and olefin sulphonates, sulphated monoglycerides, sulphated esters, sulphonated ethoxylated alcohols, sulphosuccinates, alkane sulphonates, phosphate esters, alkyl isethionates, alkyl taurates, and alkyl sarcosinates. One example of a preferred anionic surfactant is sold commercially under the name Bio-Soft N-300. It is a triethanolamine linear alkylate sulphonate composition marketed by the Stephan Company, Northfield, Ill.

The above surfactants may be used individually or in combination.

In a preferred embodiment of the present invention the polymerisation catalyst is selected with a view to additionally being the or one of the surfactants involved in the emulsification process. A particularly preferred family of catalysts which can act as surfactants are acidic condensation catalysts such as for example DBSA.

Phase inversions generally occurs when the continuous phase of a dispersion becomes the dispersed phase, or vice versa. Phase inversions in liquid/liquid dispersions generally are known in the art to be effected by one of two methods. An inversion may be caused by changing the phase ratio until there is a high enough ratio of the dispersed phase that it becomes the continuous phase. Alternatively, a transitional inversions may occur when the affinity of the surfactant for the two phases is altered in order to cause the inversion. Typically, the inversions occurring in this invention occur due to a change in the phase ratio.

Thus, the inversion method used to make emulsions, according to the invention, is carried out by forming an oil phase containing the diluted polysiloxane containing polymer and mixing and agitating the oil phase. A limited and very small amount of water is added to the oil phase in a stepwise fashion, such that an inversion occurs, and an oil-in-water emulsion is formed. Generally, the amount of water required is about 0.5-10 percent by weight based on the cumulative weight of polysiloxane containing polymer present in the oil phase. Preferably, the amount of water will be about 1-5 percent by weight based on the weight of the polysiloxane containing polymer present in the oil phase. While the water can be added in 2-4 portions, addition of water in a single portion is preferred. The initial addition of water can include the surfactant. After the desired particle size has been reached, the emulsion is diluted with the balance of water to achieve the preferred solids content.

The emulsions produced by the process of this invention can have a wide variety of polysiloxane containing polymer concentrations, particle sizes and molecular weights, including novel materials having high concentrations of large particle polysiloxane containing polymer of high molecular weight. The particle size can for example be chosen within the range 0.1 to 1000 micrometers.

The quantity of water and/or surfactant used in the initial phase inversion process may have an impact on the particle size of the final emulsion. For instance, if an emulsion is formed with the same quantity of water in two instances but in the first a large quantity of water is mixed before the phase inversion step and in the second a small quantity of water is mixed before the phase inversion step followed by mixing the remaining additional water after the phase inversion step, the first emulsion will generally have a larger particle size than the second. No matter how the water is added, the total amount of water used is generally between about 1 and 99 wt. %, preferably between about 6 and about 99 wt. %, based on the weight of the emulsion.

If desired, other materials can be added to either phase of the emulsions, for example perfumes, fillers, relaxers, colorants, thickeners, preservatives, or active ingredients such as pharmaceuticals antifoams, freeze thaw stabilizers, inorganic salts to buffer pH, and thickeners The emulsions of the present invention can generally have a silicone loading in the range of about 1 to about 94 wt. %.

The emulsions of the invention are useful in most known applications for silicone emulsions, for example in personal care applications such as on hair, skin, mucous membrane or teeth. In these applications, the silicone is lubricious and will improve the properties of skin creams, skin care lotions, moisturisers, facial treatments such as acne or wrinkle removers, personal and facial cleansers such as shower gels, liquid soap, bar soaps hand sanitizers and wipes, bath oils, perfumes, fragrances, colognes, sachets, deodorants, sun protection creams, lotions, spray, stick and wipes, Self tanning creams, lotions, spray and wipes, pre-shave and after shave lotions, after sun lotion and creams, anti-perspirant sticks, soft solid and roll ons, hand sanitizers, shaving soaps and shaving lathers. It can likewise be use in hair shampoos, rinse-off and leave-on hair conditioners, hair styling aids, such as sprays, mousses and gels, hair colorants, hair relaxers, permanents, depilatories, and cuticle coats, for example to provide styling and conditioning benefits. In cosmetics, it function as a levelling and spreading agent for pigment in make-ups, colour cosmetics, compact gel, cream and liquid foundations (w/o and o/w emulsions, anhydrous), blushes, lipsticks, lip gloss, eye liners, eye shadows, mascaras, make up removers, colour cosmetic removers and powders. It is likewise useful as a delivery system for oil and water soluble substances such as vitamins, fragrances, emollients, colorants, organic sunscreens, ceramides, pharmaceuticals and the like. When compounded into sticks, anhydrous and aqueous gels, o/w and w/o creams and lotions, aerosols and roll-ons, the emulsions of this invention impart a dry silky-smooth payout.

When used in personal care products, they are generally incorporated in amounts of about 0.01 to about 50 weight percent, preferably 0.1 to 25 wt. percent, of the personal care product. They are added to conventional ingredients for the personal care product chosen. Thus, they can be mixed with deposition polymers, surfactants, detergents, antibacterials, anti-dandruffs, foam boosters, proteins, moisturising agents, suspending agents, pacifiers, perfumes, colouring agents, plant extracts, polymers, and other conventional care ingredients.

Beyond personal care, the emulsion of the invention are useful for numerous other applications such as paints, construction applications, textile fibre treatment, leather lubrication, fabric softening, fabric care in laundry applications, healthcare, homecare, release agents, water based coatings, oil drag reduction, particularly in crude oil pipelines, lubrication, facilitation of cutting cellulose materials, and in many other areas where silicones are conventionally used. The silicone organic copolymers have particular advantages in oil drag reduction resulting from increased compatibility with hydrocarbon fluids.

EXAMPLES

The following Examples are provided so that one skilled in the art will more readily understand the invention. Unless otherwise indicated, all parts and percents are by weight and all viscosities are at 25° C. Viscosity measurements of the polymer products were carried out using a a Brookfield Viscometer, spindle 6, 10 rpm. All Particle size values were determined using a Malvern Mastersizer 2000.

Example 1

A polymer was prepared by polymerising 80 g of dimethyl hydroxyl terminated polydimethylsiloxane having 71 mPa·s at 25° C. in 80 g of trimethylsilyl terminated polydimethylsiloxane (PDMS) having a viscosity of 100 mPa·s at 25° C. using 2.4 g of dodecylbenzenesulphonic acid (DBSA) as catalyst for the condensation reaction. The polymerisation was stopped once a viscosity of 10500 mPa·s at 25° C. was reached by the addition of 1.12 g of Triethanolamine (TEA).

To 36 g of the above polymer the following surfactants were added, 1.1 g Brij® 30 and 1.9 g Brij® 35L. These were added and mixed for 30 s at 3000 rpm in Hausschild dental mixer. 1.2 g water was added and mixing was repeated for 30 s at 3000 rpm. Another 0.4 g water was added and the mixing was repeated again under the same conditions. After the second water addition the mixture had phase inverted and was diluted to a polymer content of 60%. The so obtained emulsion has a particle size of D(v, 0.5) μm=0.81 and D(v, 0.9) μm=1.14. The emulsion remained intact for a period of at least 6 months.

Brij® 30/Brij® 35L are non-ionic polyoxyethylene fatty ether (POE) surfactants. Brij® 30 is POE(4) lauryl ether with a hydrophile-lipophile balance (HLB) of 9.7. Brij® 35L is a POE (23) lauryl ether with an HLB of 16.9.

Example 2

A polymer was prepared polymerising 128 g of dimethyl hydroxyl terminated polydimethylsiloxane having a viscosity of 71 mPa·s at 25° C. in 32 g of PDMS having a viscosity of 100 mPa·s at 25° C. using 5.12 g of DBSA as the condensation catalyst. The polymerisation was stopped, once a viscosity of 171000 mPa·s at 25° C. was reached, by the addition of 2.39 g of TEA.

To 36 g of the above polymer the following surfactants were added, 1.1 g Brij® 30 and 1.9 g Brij® 35L. These were added and mixed for 30 s at 3000 rpm in Hausschild dental mixer. 0.5 g water was added mixing was repeated for 30 s at 3000 rpm. After mixing the mixture had phase inverted and was diluted to a polymer content of 60%. The so obtained emulsion has a particle size of D(v, 0.5) μm=1.77 and D(v, 0.9) μm=4.28. The emulsion remained intact for a period of at least 6 months.

Example 3

A polymer was prepared polymerising 128 g of dimethyl hydroxyl terminated polydimethylsiloxane polydimethylsiloxane having a viscosity of 71 mPa·s at 25° C. in 32 g of PDMS 100 mPa·s at 25° C. using 4.48 g of DBSA. The polymerisation was stopped once a viscosity of 171000 mPa·s at 25° C. was reached by the addition of 2.09 g of TEA.

To 36 g of the above polymer the following two surfactants were added: 1.3 g Brij® 30 and 2.4 g Brij® 35L. The surfactants and polymer were mixed for 30 s at 3000 rpm in Hausschild dental mixer. After mixing the mixture had phase inverted and was diluted to a polymer content of 60%. The so obtained emulsion has a particle size of D(v, 0.5) μm=2.07 and D(v, 0.9) μm=2.58. The emulsion remained intact for a period of at least 6 months.

Example 4

To 36 g of the polymer prepared in example 3, were added the following surfactants, 2.25 g of Arquad 16-29 Arquad® 16-29 (Akzo Nobel) and 2.25 g Tergitol®TMN-6 (Dow Chemical). No additional water was introduced as Arquad® 16-29 contains 70% by weight of water and 2.25 g TMN-6 contains 10% by weight of water. These were added and mixed for 30 s at 3000 rpm in Hausschild dental mixer. After mixing the mixture had phase inverted and was diluted to a polymer content of 60%. The so obtained emulsion has a particle size of D(v, 0.5) μm=1.23 and D(v, 0.9) μm=1.7. The emulsion remained intact for a period of at least 6 months.

Example 5

To 36 g of the polymer prepared in example 3 the following surfactants were added, 2.25 g Arquad 16-29 and 2.25 g TMN-6 together with 0.5 g water. These were mixed for 30 s at 3000 rpm in Hausschild dental mixer. After mixing the mixture had phase inverted and was diluted to a polymer content of 60%. The so obtained emulsion has a particle size of D(v, 0.5) μm=1.28 and D(v, 0.9) μm=1.96.

Arquad 16-29 is a cationic quaternary surfactant. TMN-6 is a non-ionic ethoxylated alcohol with an HLB=13.1

Example 6

To 36 g of the polymer prepared in example 3 the following surfactants were added, 1 g Biosoft N300 and 2 g Brij 30 (No additional water added). The surfactants were mixed with the polymer for 30 s at 3000 rpm in Hausschild dental mixer. After mixing the mixture had phase inverted and was diluted to a polymer content of 60%. The so obtained emulsion has a particle size of D(v, 0.5) μm=2.14 and D(v, 0.9) μm=3.14

Example 7

A polymer was prepared polymerising a 1 to 1 mixture of dimethyl hydroxyl terminated polydimethylsiloxane having a viscosity of 70 mPa·s at 25° C. and of an organic extender (Hydroseal G 250H (sold by Total) using 2.4% of DBSA as a catalyst. The polymerisation was stopped, by the addition of 1.54% of TEA, once a viscosity of 40000 mPa·s at 25° C. was reached.

To 40 g of the above polymer 1 g water was added and mixed for 30 s at 3000 rpm in a Hausschild dental mixer. After mixing the mixture had phase inverted. Additional 9 g water were added and mixing repeated under the same conditions. The mixture was then diluted to a polymer content of 40%. The so obtained emulsion has a particle size of D(v, 0.5) μm=1.46 and D(v, 0.9) μm=2.22

In this example no additional surfactant was required because the condensation catalyst DBSA used in the preparation of the polymer functioned as the required surfactant.

Example 8

40 g of the polymer prepared in example 7 and 1 g water where mixed for 30 s at 3000 rpm in Hausschild dental mixer. After mixing the mixture had phase inverted. An additional 1 g water was then added and mixing repeated under the same conditions. The mixture was then diluted to a polymer content of 50%. The so obtained emulsion has a particle size of D(v, 0.5) μm=1.75 and D(v, 0.9) μm=2.76

In this example no additional surfactant was required because the condensation catalyst DBSA used in the preparation of the polymer functioned as the required surfactant.

Example 9

A polymer was prepared by polymerising a 1:1 mixture of dimethyl hydroxyl terminated polydimethylsiloxane having a viscosity of 70 mPa·s at 25° C. and of decamethylcyclopentasiloxane which has a viscosity of 3.8 mPa·s at 25° C. using 2.4% of DBSA as a catalyst. The polymerisation was stopped once a viscosity of 27000 mPa·s at 25° C. was reached by the addition of 1.54% of TEA. In this case the DBSA catalyst used in the polymerisation step above additionally functioned as the surfactant in the preparation of emulsions as described below.

0.3 g water was added to 36 g of the above polymer and mixed for 30 s at 3000 rpm in a Hausschild dental mixer. Another 0.9 g water were subsequently added and mixed under the same conditions. After mixing the mixture had phase inverted. A further 1.9 g of water was then added and mixing repeated under the same conditions. The resulting mixture was then diluted to a polymer content of 50%. The resulting emulsion has a particle size of D(v, 0.5) μm=1.46 and D(v, 0.9) μm=2.34.

Example 10

A polymer was prepared by polymerising a 4:1 mixture of dimethyl hydroxyl terminated polydimethylsiloxane having a viscosity of 70 mPa·s at 25° C. in an organic extender (Hydroseal G 250H) using 2.4% g of DBSA as a catalyst. The polymerisation was stopped once a viscosity of 40000 mPa·s at 25° C. was reached by the addition of 1.54% g of TEA.

1 g water was added to 40.2 g of the above polymer and mixed for 30 s at 3000 rpm in a Hausschild dental mixer. After mixing the mixture had phase inverted. An additional 1.1 g of water was added and mixing repeated under the same conditions. The resulting mixture was then diluted to a polymer content of 50%. The so obtained emulsion has a particle size of D(v, 0.5) μm=1.46 and D(v, 0.9) μm=2.26.

Example 11

1.1 g water was added and mixed with 40.2 g of the polymer prepared in Example 10 for 30 s at 3000 rpm in a Hausschild dental mixer. After mixing the resulting mixture had phase inverted. An additional 1.4 g of water was added and mixing repeated under the same conditions. A still further 2.5 g of water was subsequently added and mixing repeated under the same conditions. The resulting mixture was then diluted to a polymer content of 80%. The resulting viscous cream (emulsion) had a particle size of D(v, 0.5) μm=1.26 and D(v, 0.9) μm=1.84.

Example 12

A polymer was prepared by polymerising a 1:1 mixture of dimethyl hydroxyl terminated polydimethylsiloxane having a viscosity of 70 mPa·s at 25° C. in cosmetic grade organic fluid (Isopar® M, sold by Exxon) using 20 parts per million (ppm) of a phosphonitrile catalyst. The polymerisation was stopped once a viscosity of 51000 mPa·s at 25° C. was reached by the addition of trihexylamine. The polymer had a number average molecular weight of 198000 g/mol and a polydispersity index of 1.54.

1.1 g Volpo® L3, 1.6 g Volpo® L23 and 1.1 g water was added to 50.2 g of the polymer prepared as described above and the resulting mixture was mixed for 60 s at 3000 rpm in a Hausschild dental mixer. An additional 1.0 g of water was added and mixing repeated under the same conditions. A still further 1.0 g of water was added and the same mixing process was repeated again. After mixing the resulting mixture had phase inverted. Further 2.2 g of water was subsequently added and mixing repeated under the same conditions. The resulting mixture was then diluted to a polymer/fluid content of 50%. The resulting emulsion had a particle size of D(v, 0.1) μm=1.23, D(v, 0.5) μm=2.67 and D(v, 0.9) μm=5.01 and henceforth is referred to as sample 12.1 emulsion.

The resulting emulsion was introduced into a selection of personal care formulations, including fruity gel blushers, eye shadow, water in oil skin creams, hair care conditioners, leave-on and the following:—

Cold Mix Lotion

This lotion was prepared with the ingredients depicted in Table 12(a) below by initially mixing the phase B ingredients together and then introducing phase A into the phase B and then mixing the resulting product until it is homogeneous.

TABLE 12(A)

| Ingredients | INCI Name | % |
|---|---|---|
| Phase A | | |
| Sample 12.1 emulsion | | 20 |
| Phase B | | |
| Water | | 78 |
| Phenochem | Phenoxyethanol (and) Methylparaben (and) Butylparaben (and) Ethylparaben (and) Propylparaben (and) Isobutylparaben | 1 |
| Keltrol | Xanthan Gum | 1 |

It was found that the sample 12.1 emulsion could be easily incorporated in a lotion type product and the resulting lotion was found to have a significant impact on sensory profile, in upon testing using 18 panelists. Significant differences in >95% of results was found for speed of absorption, gloss, film residue, greasiness. This indicates that sample 12.1 emulsion could significantly impact the sensory of lotion prepared as described herein, making it richer and more nourishing.

Water in Silicone Skin Cream

The above was prepared using the ingredients identified in Table 12(b) below:—

TABLE 12(B)

| Ingredients | INCI Name | % |
|---|---|---|
| Phase A | | |
| Dow Corning ® 5225C Formulation Aid | Cyclopentasiloxane (and) PEG/PPG-18/18 Dimethicone | 10 |
| Dow Corning ® 245 Fluid | Cyclopentasiloxane | 18.6 |
| Phase B | | |
| Sample 12.1 emulsion | | 2.3 |
| Sodium Chloride | | 2 |
| Water | | 67.1 |
| Viscosity: Spindle 7, 20 rpm | | 11800 mPa · s |

The ingredients of phase A were mixed together. The ingredients of phase B were mixed together. Phase B was then introduced dropwise into the phase A mixture whilst continuously agitation the resulting mixture and finally the resulting mixture was homogenized using a high shear mixer.

Sensory tests were carried out using 18 panelists to determine the performance of the resulting cream as described above, containing 2.3% by weight of Sample 12.1 emulsion in comparison to an identical cream in the absence of the sample 12.1 emulsion. Significant differences >95% were identified with respect to speed of absorption, gloss, film residue and greasiness demonstrating that the presence of Sample 12.1 emulsion at levels as low as 2.3% impact significantly the sensory of the cream making it richer and more nourishing.

Opaque Shampoo

The above was prepared using the ingredients identified in Table 12(c) below:—

TABLE 12(C)

| Ingredients | INCI Name | % |
|---|---|---|
| Phase A | | |
| Water | | 60.5 |
| Crothix liquid | PEG-150 Pentaerythrityl Tetrastearate and PEG-6 Caprylic/Capric Glycerides and Water | 1.5 |
| Empicol ESB-3 | Sodium Laureth Sulfate | 12 |
| Texapon A 400 | Ammonium Lauryl Sulfate | 10 |
| Amonyl 380BA | Cocamidopropyl Betaine | 8 |
| Comperlan KD | Cocamide DEA | 4 |
| Phase B | | |
| Sample 12.1 emulsion | | 4 |
| Phase C | | |
| Citric Acid | | q.s |
| Nipaguard DMDMH | DMDM Hydantoin | q.s |
| Viscosity: Spindle 7, 20 rpm | | 41600 mPa · s |

Water was heated to 70° C. The ingredients of phase A were mixed together. Phase B was inter-mixed with phase A with gentle mixing and then phase C was introduced and the resulting composition was allowed to cool.

Several panelists were asked to comb slightly bleached hair tresses washed with the resulting shampoo. The time to wet detangle the hair tresses was measured. As a direct comparison the panelists also undertook the same process with slightly bleached hair tresses using the same shampoo formulation without any emulsion. The results indicate a slight decrease in the detangling time with the shampoo containing the sample 12.1 emulsion. This indicates an improvement in the conditioning effect in the shampoo when the emulsions in accordance with the present invention were present.

Example 13

A range of polymers Examples 13(a) to 13(i) were prepared by polymerising mixtures of dimethyl hydroxyl terminated polydimethylsiloxane having a viscosity of 70 mPa·s at 25° C. and sunflower seed oil using DBSA as a catalyst (as indicated in Table 13(a)). All ingredients were mixed at 1500 rpm for 30 s (Hausschild dental mixer). The polymerisation was stopped after different times by adding TEA and mixing again under the same conditions.

TABLE 13A

| | Example | | | | | | | | |
|---|---|---|---|---|---|---|---|---|---|
| | a | b | c | d | e | f | g | h | I |
| Siloxane (g) | 45 | 45 | 45 | 40 | 40 | 40 | 35 | 35 | 35 |
| Sunflower Oil (g) | 5 | 5 | 5 | 10 | 10 | 10 | 15 | 15 | 15 |
| DBSA (g) | 1.5 | 2 | 2.5 | 1.5 | 2 | 2.5 | 1.5 | 2 | 2.5 |
| TEA (g) | 0.94 | 1.25 | 1.56 | 0.94 | 1.25 | 1.56 | 0.94 | 1.25 | 1.56 |
| Reaction time (min) | 35 | 31 | 20 | 34 | 29 | 21 | 33 | 29 | 21 |

Subsequent to completion of polymerisation, emulsions were prepared using the following process:—
Firstly 1 g water was directly added to the polymerisation product and the resulting mixture was mixed at 3000 rpm for 60 s. The water addition step was repeated was repeated with 1 g water added and mixed at 3000 rpm for 60 s, then, a further 8 g of water was added and mixed at 3000 rpm for 60 s and finally 40 g of water was added and mixed at 1500 pm for 30 s.

The resulting emulsions were analysed for Molecular weight (obtained by GPC) and cyclic siloxane content ($D_4$-$D_{12}$) by gas chromatography. The results are provided in Table 13(b) below

TABLE 13(B)

| | Example | | | | | | | | |
|---|---|---|---|---|---|---|---|---|---|
| | a | b | c | d | e | f | g | h | i |
| D(v, 0.1) Mm | 0.5 | 0.33 | 0.6 | 0.53 | 0.36 | 0.26 | 0.21 | 0.22 | 0.23 |
| D(v, 0.5) Mm | 0.77 | 2.49 | 0.99 | 0.94 | 1.14 | 1.7 | 0.77 | 1.09 | 1.67 |
| D(v, 0.9) Mm | 1.05 | 6.11 | 1.61 | 1.48 | 1.91 | 3.8 | 1.91 | 2.39 | 4.01 |
| Mn kg/mol | 82 | 158 | 229 | 98 | 162 | 211 | 129 | 174 | 205 |
| Mw kg/mol | 112 | 220 | 312 | 142 | 229 | 296 | 183 | 252 | 300 |
| $D_4$ (%) | 0.06 | 0.09 | 0.09 | 0.07 | 0.07 | 0.07 | 0.05 | 0.06 | 0.06 |
| $D_5$ (%) | 0.04 | 0.06 | 0.06 | 0.05 | 0.05 | 0.05 | 0.04 | 0.04 | 0.04 |
| $D_6$ (%) | 0.05 | 0.07 | 0.06 | 0.06 | 0.06 | 0.05 | 0.05 | 0.05 | 0.05 |
| $D_7$ (%) | 0.06 | 0.07 | 0.06 | 0.07 | 0.07 | 0.06 | 0.06 | 0.06 | 0.05 |
| $D_8$ (%) | 0.05 | 0.07 | 0.05 | 0.06 | 0.06 | 0.05 | 0.05 | 0.05 | 0.04 |
| $D_9$ (%) | 0.05 | 0.06 | 0.05 | 0.06 | 0.05 | 0.05 | 0.05 | 0.05 | 0.04 |
| $D_{10}$ (%) | 0.04 | 0.05 | 0.04 | 0.05 | 0.05 | 0.04 | 0.05 | 0.05 | 0.04 |
| $D_{11}$ (%) | 0.04 | 0.05 | 0.03 | 0.04 | 0.04 | 0.04 | 0.04 | 0.04 | 0.03 |
| $D_{12}$ (%) | 0.04 | 0.05 | 0.04 | 0.04 | 0.04 | 0.04 | 0.04 | 0.04 | 0.04 |

The resulting emulsions prepared in accordance with the above and identified as Example 13b, Example 13e and Example 13h were introduced into a selection of personal care formulations, including fruity gel blushers, water in oil and water in silicone skin creams, hair care shampoo, leave-on, and the following:—

Ethnic Hair Care: Conditioner

The above was prepared using the ingredients identified in Table 13(c) below:—

TABLE 13(C)

| Ingredients | INCI Name | % |
|---|---|---|
| Phase A | | |
| Water | | 79.47 |
| Natrosol 250 HHR | Hydroxyethylcellulose | 1.5 |
| Arquad 16-29 | Cetrimonium Chloride | 0.7 |
| Phase B | | |
| Lanette Wax O | Cetearyl Alcohol | 4 |
| Arlacel 165 | Glyceryl Stearate and PEG-100 Stearate | 1 |
| Phase C | | |
| Propylene Glycol | | 4 |
| Glycerin | | 4 |
| Phase D | | |
| Gluadin W20 | Hydrolyzed Wheat Protein | 1 |
| Germaben II | Propylene Glycol and Diazolidinyl Urea and Methylparaben and Propylparaben | 1 |
| Phase E | | |
| Example 13e Emulsion | | 3.33 |
| Viscosity: Spindle 7, 20 rpm | | 45200 mPa · s |

The ingredients of phase A were mixed together and then heated to 75° C. Phase B was then added whilst mixing and the mixture was allowed to commence cooling. Phase C was then introduced and the resulting mixture was allowed to cool to 50° C. Phase D was then added and the mixture was cooled to room temperature. Phase E was then added and finally water was introduced to compensate for water loss during heating phase.

Several panelists were asked to comb slightly bleached hair tresses washed with the resulting conditioner to determine the time taken to detangle the wet hair. In comparison the participants had to comb slightly bleached hair tresses which had been washed with the same conditioner formulation without any emulsion. The results indicate a significant decrease (>99%) into the detangling time when using the conditioner containing example 13e emulsion indicating a positive impact on hair conditioning.

Shower Gel

The above was prepared using the ingredients identified in Table 13(d) below:—

TABLE 13(D)

| Ingredients | INCI Name | % |
|---|---|---|
| Phase A | | |
| Empicol ESB-3 | Sodium Laureth Sulfate | 30 |
| Oramix NS10 | Decyl Glucoside | 5 |
| Amonyl 380BA | Cocamidopropyl Betaine | 10 |
| Brij 30 | Laureth-4 | 2 |
| Sepigel 305 | Polyacrylamide and C13-14 | 2 |

TABLE 13(D)-continued

| Ingredients | INCI Name | % |
|---|---|---|
| Water | Isoparaffin and Laureth-7 | 42.7 |
| Phase B | | |
| Example 13e Emulsion | | 8.3 |
| Phase C | | |
| Sodium Chloride | | q.s |
| Viscosity: Spindle 5, 100 rpm | | 4000 mPa · s |

The ingredients of phase A were initially mixed until homogeneous, after which phase B was introduced whilst mixing was continued. Phase C was then introduced to adjust the viscosity of the final mixture to the required value. It was found that emulsions in accordance with the present invention, such as example 13e emulsion, can be easily added to shower gel formulations and provide stable formulations.

Smooth Stay Shadow (Eye Make-Up)

The above was prepared using the ingredients identified in Table 13(e) below:—

TABLE 13(E)

| Ingredients | INCI Name | % |
|---|---|---|
| Phase A | | |
| Glycerin | | 8 |
| Propylene Glycol | | 8 |
| Phase B | | |
| Covacryl RH | Sodium Polyacrylate | 0.7 |

TABLE 13(E)-continued

| Ingredients | INCI Name | % |
|---|---|---|
| Phase C | | |
| Water | | 42 |
| Nipaguard DMDMH | DMDM Hydantoin | 0.3 |
| Phase D | | |
| Example 13b Emulsion | | 6 |
| Covacryl E14 | Acrylates Copolymer | 20 |
| Phase E | | |
| Covapearl light brown 830 AS | Mica and CI 77491 and Triethoxycaprylysilane | 4 |
| Covapearl satin 931 AS | Mica and CI 77891 and Triethoxycaprylysilane | 11 |

Phase B was first dispersed in phase A. The resulting mixture of Phases A and B were then mixed into phase C under agitation. Phase D was then added to the mixture and was mixed until homogeneous. Finally phase E was added and the final formulation was mixed until homogeneous.

It was found that that emulsions such as Example 13b emulsion as hereinbefore described can be easily incorporated into a eye shadow formulations with high pigment levels. 18 panelists compared the eye shadow formulation with example 13b emulsion in comparison with the same formulation in the absence of said emulsion. It was identified that the formulation containing Example 13b emulsion increased the tackiness of the formulation without significantly impacting the gloss and spreadability of the formulation thereby improving adhesion and retention of the formulation on the skin.

Skinshield—Water in Oil Skin Cream

The above was prepared using the ingredients identified in Table 13(f) below:—

TABLE 13(F)

| Ingredients | INCI Name | % |
|---|---|---|
| Phase A | | |
| Dow Corning ® 5200 Formulation Aid | Lauryl PEG/PPG-18/18 Methicone | 2 |
| Mineral Oil | | 8 |
| Dow Corning ® 2-1184 Fluid | Trisiloxane and Dimethicone | 4.5 |
| Dow Corning ® 9040 Silicone Elastomemr Blend | Cyclopentasiloxane and Dimethicone Crosspolymer | 5 |
| Escalol 557 | Ethylhexyl Methoxycinnamate | 2 |
| Dekaben (as sold by Jan Dekker company) | Phenoxyethanol and Methylparaben and Ethylparaben and Propylparaben and Butylparaben | 0.5 |
| Phase B | | |
| Water | | 61.94 |
| Sodium Chloride | | 1 |
| Propylene Glycol | | 5 |
| Glycofilm | Biosaccharide Gum-4 | 5 |
| Example 13h Emulsion | | 5 |
| Phase C | | |
| D&C Red 28 (0.5% in water) | D&C red 28/LCW | 0.06 |
| Viscosity: Spindle 7, 20 rpm | | 27400 mPa · s |

The ingredients of phase A were mixed until homogeneous. The phase B ingredients were then mixed together with sufficient agitation to obtain a homogeneous mixture. Phase C was then introduced into phase B whilst mixing was continued and then the phases B and C mixture was introduced into phase A whilst mixing. After the complete addition mixing was continued for a further 15 minutes Cold Mix Lotion The above was prepared using the ingredients identified in Table 13(g) below:—

TABLE 13(G)

| Ingredients | INCI Name | % | % |
|---|---|---|---|
| Phase A | | | |
| Example 13h Emulsion | | — | 20 |
| Phase B | | | |
| Water | | 78 | 78 |
| Phenochem | Phenoxyethanol (and) Methylparaben (and) Butylparaben (and) Ethylparaben (and) Propylparaben (and) Isobutylparaben | 1 | 1 |
| Keltrol | Xanthan Gum | 1 | 1 |

The ingredients of phase B were initially mixed together and then the resulting mixture was introduced into phase A and was mixed until homogeneous.

Example 14

A polymer was prepared by polymerising a 1:1 mixture of dimethyl hydroxyl terminated polydimethylsiloxane having a viscosity of 70 mPa·s at 25° C. and an organic extender (Hydroseal G 250H) using 20 ppm of a phosphonitrile catalyst. The polymerisation was stopped once a viscosity of 100000 mPa·s at 25° C. was reached by the addition of trihexylamine. The polymer had a number average molecular weight of 235000 g/mol and a polydispersity index of 1.48.

1.75 g Volpo® L4, 1.25 g and Volpo® L23 was added to 30 g of the polymer/extender blend described above and mixed for 20 s at 3000 rpm in a Hausschild dental mixer. An additional 2.0 g of water was added and mixing repeated under the same conditions. Further additions of 2.0 g of water were repeated four more times. The resulting mixture was then diluted with additional 30 g of water.

The above emulsion was evaluated in a fabric softener consisting of:
55.6 g Tetranyl L1/90 standard
8 g MgCl$_2$.6H$_2$O solution@20%
936.4 g of water
Total=1000 g→5% active Quat The Tetranyl L1/90 standard was first melted at 55° C. The resulting liquid was then poured whilst being continuously stirred into in hot water and the resulting mixture was allowed to cool with continued stirring. During the cooling period, again with continuous stirring the magnesium chloride salt and the emulsion prepared in accordance with the invention were introduced.

The fabric (cotton towels) was treated by adding the softener using a Miele washing machine and a washing it with commericial detergent powder (DASH). Softness of towels was determined in a panel test and rated from 1-10 (10=softest). While the fabric softener described above was rated at 5.0, the fabric softener containing the emulsion in accordance with the present invention was rated at 5.5.

The water absorbency of the treated fabric was tested by dropping a 2 cm*2 cm sample into 250 ml water. The time until the fabric is sinking is recorded. The result was 9 s for the sample treated with softener containing the emulsion as described above and 128 s for a sample treated with a softener only, showing therefore improved water absorbency.

The invention claimed is:

1. A method of making silicone oil-in-water emulsions containing a polysiloxane containing polymer, said method comprising the steps of:
   (i) preparing a polysiloxane containing polymer by the polymerisation of siloxane containing monomers and/or oligomers in the presence of an inert organopolysiloxane and/or an organic fluid, a suitable catalyst and optionally an end-blocking agent, wherein the polysiloxane containing polymer is of the following general formula

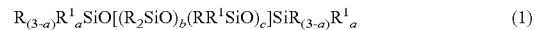

$$R_{(3-a)}R^1_a SiO[(R_2SiO)_b(RR^1SiO)_c]SiR_{(3-a)}R^1_a \quad (1)$$

wherein each R is the same or different and is an alkyl group containing 1 to 8 carbon atoms or a phenyl group; $R^1$ is a hydroxy group, a hydrolysable group, or an unsaturated organic group; a is zero or 1; b is an integer; c is zero or an integer; and the sum of b+c is equal to a value of at least 500;
   (ii) optionally quenching the polymerisation process; wherein the inert fluid is retained within the resulting polysiloxane containing polymer in an amount of from 5 to 70% w/w;
   (iii) optionally introducing one or more surfactants into the polysiloxane containing polymer to form a homogenous oil phase;
   (iv) adding water to the homogenous oil phase to form a water-in-oil emulsion, the water being added in an amount of 0.1 to 10 percent by weight based on the total oil phase weight;
   (v) applying shear to the water-in-oil emulsion to cause inversion of the water-in-oil emulsion to an oil-in-water emulsion; and
   (vi) optionally diluting the oil-in-water emulsion by adding more water.

2. The method according to claim 1, wherein the inert fluid is an organic extender and/or plasticizer and/or a natural oil.

3. The method according to claim 1, wherein the inert fluid is a cyclic siloxane having from 2 to 20 silicon atoms.

4. The method according to claim 1, wherein the inert fluid comprises a silicone cyclic and the silicone is a polydimethyl gum.

5. The method according to claim 1, wherein the inert fluid is a trialkylsilyl terminated polydialkylsiloxane having a viscosity of from 0.65 to 10000 mPa·s at 25° C.

6. The method according to claim 1, wherein the polysiloxane containing polymer is prepared via a polymerisation process selected from the group of polycondensation, chain extension, polyaddition, and ring opening.

7. The method according to claim 1, wherein the catalyst is part of the surfactant used for emulsification.

8. The method according to claim 7, wherein the polysiloxane containing polymer is prepared via a polycondensation reaction and the catalyst is dodecylbenzenesulphonic acid.

9. The method according to claim 1, wherein the homogenous oil phase is from 1000 to 100000 mPa·s at 25° C.

10. The method according to claim 1, wherein the sum of b+c is equal to a value of at least 1500.

11. The method according to claim 1, wherein the inert fluid is a cyclic siloxane having from 2 to 20 silicon atoms.

12. The method according to claim 1, wherein the inert fluid is a trialkylsilyl terminated polydialkylsiloxane having a viscosity of from 0.65 to 10000 mPa·s at 25° C.

13. A method of making silicone oil-in-water emulsions containing a polysiloxane containing polymer, said method comprising the steps of:
(i) preparing a polysiloxane containing polymer by the polymerisation of siloxane containing monomers and/or oligomers in the presence of an inert fluid, wherein the inert fluid has a viscosity of from 0.65 mPa·s to 10000 mPa·s at 25° C. and is selected from an organopolysiloxane extender or plasticiser, an organic extender or plasticiser, or a cyclic siloxane comprising between 3 and 20 silicon atoms, a catalyst and optionally an end-blocking agent, wherein the polysiloxane containing polymer is of the following general formula

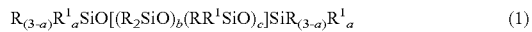  (1)

wherein each R is the same or different and is an alkyl group containing 1 to 8 carbon atoms or a phenyl group; $R^1$ is a hydroxy group, a hydrolysable group, or an unsaturated organic group; a is zero or 1; b is an integer; c is zero or an integer; and the sum of b+c is equal to a value of at least 200;
(ii) optionally quenching the polymerisation process; wherein the inert fluid is retained within the resulting polysiloxane containing polymer in an amount of from 5 to 70% w/w;
(iii) optionally introducing one or more surfactants into the polysiloxane containing polymer to form a homogenous oil phase;
(iv) adding water to the homogenous oil phase to form a water-in-oil emulsion, the water being added in an amount of 0.1 to 10 percent by weight based on the total oil phase weight;
(v) applying shear to the water-in-oil emulsion to cause inversion of the water-in-oil emulsion to an oil-in-water emulsion; and
(vi) optionally diluting the oil-in-water emulsion by adding more water.

14. The method according to claim 1, wherein the polysiloxane is a polydimethyl gum.

15. The method according to claim 1, wherein the polysiloxane containing polymer is prepared via a polymerisation process selected from the group of polycondensation, chain extension, polyaddition, and ring opening, and the catalyst is part of the surfactant used for emulsification.

16. The method according to claim 1, wherein the inert fluid is retained within the resulting polysiloxane containing polymer in an amount of from 5 to 60% w/w.

* * * * *